United States Patent
Falsafi et al.

(10) Patent No.: US 9,943,465 B2
(45) Date of Patent: Apr. 17, 2018

(54) METHODS OF USING A DENTAL COMPOSITION HAVING AN ACIDIC COMPONENT AND A PHOTOBLEACHABLE DYE

(75) Inventors: Afshin Falsafi, Woodbury, MN (US); Joel D. Oxman, Minneapolis, MN (US); Tiffany T. Ton, Woodbury, MN (US); Joan V. Brennan, Sierra Madre, CA (US); David K. Cinader, Jr., Walnut, CA (US); Bhaskar V. Velamakanni, Woodbury, MN (US); Sumita B. Mitra, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1675 days.

(21) Appl. No.: 12/517,739

(22) PCT Filed: Dec. 12, 2007

(86) PCT No.: PCT/US2007/087192
§ 371 (c)(1),
(2), (4) Date: Jun. 4, 2009

(87) PCT Pub. No.: WO2008/076739
PCT Pub. Date: Jun. 26, 2008

(65) Prior Publication Data
US 2010/0015578 A1    Jan. 21, 2010

Related U.S. Application Data

(60) Provisional application No. 60/869,741, filed on Dec. 13, 2006.

(51) Int. Cl.
*A61C 5/00*    (2017.01)
*A61K 6/00*    (2006.01)
*A61K 6/083*    (2006.01)

(52) U.S. Cl.
CPC .......... *A61K 6/0017* (2013.01); *A61K 6/0023* (2013.01); *A61K 6/083* (2013.01)

(58) Field of Classification Search
CPC ..... A61K 6/0017; A61K 6/0023; A61K 6/083
USPC ..... 433/9, 215, 216, 89, 226, 228.1; 106/35; 523/113–118; 522/13, 47, 48
See application file for complete search history.

(56) References Cited

U.S. PATENT DOCUMENTS

| | | | |
|---|---|---|---|
| 3,655,605 A | 4/1972 | Smith | |
| 3,797,690 A * | 3/1974 | Taylor et al. | 428/35.4 |
| 4,016,124 A | 4/1977 | Crisp et al. | |
| 4,054,598 A | 10/1977 | Blum et al. | |
| 4,070,321 A | 1/1978 | Goretta et al. | |
| 4,089,830 A | 5/1978 | Tezuka et al. | |
| 4,143,018 A | 3/1979 | Crisp et al. | |
| 4,204,978 A | 5/1980 | William et al. | |
| 4,259,075 A | 3/1981 | Yamauchi et al. | |
| 4,259,117 A | 3/1981 | Yamauchi et al. | |
| 4,267,108 A | 5/1981 | Blum et al. | |
| 4,298,738 A | 11/1981 | Lechtken et al. | |
| 4,302,381 A | 11/1981 | Omura et al. | |
| 4,304,734 A | 12/1981 | Jary et al. | |
| 4,324,744 A | 4/1982 | Lechtken et al. | |
| 4,327,039 A | 4/1982 | Blum et al. | |
| 4,342,677 A | 8/1982 | Muramatsu et al. | |
| 4,347,233 A | 8/1982 | Yamauchi et al. | |
| 4,356,296 A | 10/1982 | Griffith et al. | |
| 4,360,605 A | 11/1982 | Schmitt et al. | |
| 4,368,403 A | 1/1983 | Lewis | |
| 4,376,835 A | 3/1983 | Schmitt et al. | |
| 4,383,052 A | 5/1983 | Higo et al. | |
| 4,385,109 A | 5/1983 | Lechtken et al. | |
| 4,407,761 A | 10/1983 | Blum et al. | |
| 4,499,251 A | 2/1985 | Omura et al. | |
| 4,503,169 A | 3/1985 | Randklev | |
| 4,507,407 A | 3/1985 | Kluger | |
| 4,526,728 A | 7/1985 | Finke et al. | |
| 4,537,940 A | 8/1985 | Omura et al. | |
| 4,539,382 A | 9/1985 | Omura et al. | |
| 4,612,384 A | 9/1986 | Omura et al. | |
| 4,621,077 A | 11/1986 | Rosini et al. | |
| 4,642,126 A | 2/1987 | Zador et al. | |
| 4,648,843 A | 3/1987 | Mitra | |
| 4,650,847 A | 3/1987 | Omura et al. | |
| 4,652,274 A | 3/1987 | Boettcher et al. | |
| 4,665,217 A | 5/1987 | Reiners et al. | |
| 4,678,436 A | 7/1987 | Kondo | |
| 4,687,767 A | 8/1987 | Bosies et al. | |
| 4,695,251 A | 9/1987 | Randklev | |
| 4,710,523 A | 12/1987 | Lechtken et al. | |
| 4,719,149 A | 1/1988 | Aasen et al. | |
| 4,737,593 A | 4/1988 | Ellrich et al. | |
| 4,752,338 A | 6/1988 | Reiners et al. | |
| 4,755,620 A | 7/1988 | Iwamoto et al. | |
| 4,792,632 A | 12/1988 | Ellrich et al. | |
| 4,814,514 A | 3/1989 | Yokota et al. | |
| 4,816,495 A | 3/1989 | Blackwell | |
| 4,872,936 A | 10/1989 | Engelbrecht | |
| 4,922,007 A | 5/1990 | Kieczykowski et al. | |
| 4,939,283 A | 7/1990 | Yokota et al. | |

(Continued)

FOREIGN PATENT DOCUMENTS

DE    2537463 A1    4/1976
DE    35 36076 A1    4/1987
(Continued)

OTHER PUBLICATIONS 1-aminoanthraquinone , May 1996, Tokyo, Japan.*
(Continued)

Primary Examiner — Yogesh Patel

(57) ABSTRACT

Methods of using a dental composition having a photobleachable dye and an acidic component with a pKa of less than 4.5 are disclosed. The photobleachable dye is selected from the group consisting of aminoanthraquinone dyes, azo dyes, and combinations thereof. The aged color of the dental composition is substantially the same as the color of the dental composition immediately after hardening.

22 Claims, No Drawings

(56) References Cited

U.S. PATENT DOCUMENTS

| | | |
|---|---|---|
| 5,019,651 A | 5/1991 | Kieczykowski |
| 5,026,902 A | 6/1991 | Fock et al. |
| 5,055,497 A | 10/1991 | Okada et al. |
| 5,063,257 A | 11/1991 | Akahane et al. |
| 5,076,844 A | 12/1991 | Fock et al. |
| 5,130,347 A | 7/1992 | Mitra |
| 5,154,762 A | 10/1992 | Mitra et al. |
| 5,172,809 A | 12/1992 | Jacobs et al. |
| 5,180,757 A | 1/1993 | Lucey |
| 5,227,413 A | 7/1993 | Mitra |
| 5,254,198 A | 10/1993 | Kawashima et al. |
| 5,256,447 A | 10/1993 | Oxman et al. |
| 5,324,862 A | 6/1994 | Yokota et al. |
| 5,332,854 A | 7/1994 | Yokota et al. |
| 5,338,769 A | 8/1994 | Miyamoto |
| 5,354,827 A | 10/1994 | Muller et al. |
| 5,367,002 A | 11/1994 | Huang et al. |
| 5,501,727 A | 3/1996 | Wang et al. |
| 5,510,517 A | 4/1996 | Dauer et al. |
| 5,520,725 A | 5/1996 | Kato et al. |
| 5,525,648 A | 6/1996 | Aasen et al. |
| 5,530,038 A | 6/1996 | Yamamoto et al. |
| 5,545,676 A | 8/1996 | Palazzotto et al. |
| 5,554,030 A | 9/1996 | Ario et al. |
| 5,575,645 A | 11/1996 | Jacobs et al. |
| 5,593,303 A | 1/1997 | Cohen et al. |
| 5,608,042 A | 3/1997 | Himeno |
| 5,629,361 A | 5/1997 | Nakabayashi et al. |
| 5,645,429 A | 7/1997 | Blackwell et al. |
| 5,648,491 A | 7/1997 | Dauer et al. |
| 5,658,963 A | 8/1997 | Qian et al. |
| 5,700,875 A | 12/1997 | Zeng et al. |
| 5,710,194 A | 1/1998 | Hammesfahr et al. |
| 5,766,012 A | 6/1998 | Rosembaum et al. |
| 5,834,532 A | 11/1998 | Yamamoto et al. |
| 5,856,373 A | 1/1999 | Kaisaki et al. |
| 5,859,089 A | 1/1999 | Qian |
| 5,871,360 A | 2/1999 | Kato |
| 5,919,836 A | 7/1999 | Reinhardt |
| 5,919,846 A | 7/1999 | Batlaw |
| 5,925,715 A | 7/1999 | Mitra |
| 5,962,550 A | 10/1999 | Akahane et al. |
| 5,965,632 A | 10/1999 | Orlowski et al. |
| 5,980,253 A | 11/1999 | Oxman et al. |
| 6,004,390 A | 12/1999 | Pflug et al. |
| 6,030,606 A | 2/2000 | Holmes |
| 6,050,815 A | 4/2000 | Adam et al. |
| 6,084,004 A | 7/2000 | Weinmann et al. |
| 6,089,861 A | 7/2000 | Kelly et al. |
| 6,126,922 A | 10/2000 | Rozzi et al. |
| 6,172,131 B1 | 1/2001 | Moszner et al. |
| 6,174,935 B1 | 1/2001 | Matsunae et al. |
| 6,187,833 B1 | 2/2001 | Oxman et al. |
| 6,187,836 B1 | 2/2001 | Oxman et al. |
| 6,213,767 B1 | 4/2001 | Dixon et al. |
| 6,217,644 B1 | 4/2001 | Matsunae |
| 6,251,963 B1 | 6/2001 | Kohler et al. |
| 6,306,926 B1 | 10/2001 | Bretscher et al. |
| 6,309,215 B1 | 10/2001 | Phan et al. |
| 6,331,080 B1 * | 12/2001 | Cole ............ C09J 11/06 385/147 |
| 6,350,839 B2 | 2/2002 | Moszner et al. |
| 6,355,704 B1 | 3/2002 | Nakatsuka et al. |
| 6,387,979 B1 | 5/2002 | Hino |
| 6,387,981 B1 | 5/2002 | Zhang et al. |
| 6,387,982 B1 | 5/2002 | Blackwell |
| 6,444,725 B1 * | 9/2002 | Trom et al. ............ 523/118 |
| 6,458,868 B1 | 10/2002 | Okada et al. |
| 6,472,454 B1 | 10/2002 | Qian |
| 6,482,871 B1 | 11/2002 | Aasen et al. |
| 6,506,816 B1 | 1/2003 | Ario et al. |
| 6,528,555 B1 * | 3/2003 | Nikutowski et al. ...... 523/116 |
| 6,565,873 B1 | 5/2003 | Shefer et al. |
| 6,566,413 B1 | 5/2003 | Weinmann et al. |
| 6,572,693 B1 | 6/2003 | Wu et al. |
| 6,575,752 B1 | 6/2003 | Pflug |
| 6,624,236 B1 | 9/2003 | Bissinger et al. |
| 6,669,927 B2 | 12/2003 | Trom et al. |
| 6,691,715 B2 | 2/2004 | Matz et al. |
| 6,765,036 B2 | 7/2004 | Dede et al. |
| 6,765,038 B2 | 7/2004 | Mitra |
| 6,830,450 B2 | 12/2004 | Knopp et al. |
| 6,869,984 B2 | 3/2005 | Kawashima |
| 6,916,858 B2 | 7/2005 | Kojima |
| 6,939,901 B2 | 9/2005 | Nakatsuka |
| 6,960,079 B2 * | 11/2005 | Brennan et al. ............... 433/9 |
| 6,982,288 B2 | 1/2006 | Mitra et al. |
| 6,994,551 B2 | 2/2006 | Wang et al. |
| 7,090,721 B2 | 8/2006 | Craig et al. |
| 7,090,722 B2 | 8/2006 | Budd et al. |
| 7,129,281 B2 | 10/2006 | Fujiwara |
| 7,137,812 B2 | 11/2006 | Cleary |
| 7,156,911 B2 | 1/2007 | Kangas et al. |
| 7,173,074 B2 | 2/2007 | Mitra et al. |
| 7,186,950 B1 | 3/2007 | Fisher |
| 7,250,452 B2 | 7/2007 | Falsafi |
| 7,262,228 B2 | 8/2007 | Oxman |
| 7,374,420 B2 | 5/2008 | Brennan |
| 7,473,096 B2 | 1/2009 | Cinader, Jr. |
| 7,541,393 B2 | 6/2009 | Mitra |
| 7,632,098 B2 | 12/2009 | Falsafi et al. |
| 7,649,029 B2 | 1/2010 | Kolb et al. |
| 7,841,464 B2 | 11/2010 | Cinader, Jr. |
| 7,910,632 B2 | 3/2011 | Cinader, Jr. |
| 2001/0044513 A1 | 11/2001 | Moszner et al. |
| 2002/0015682 A1 | 2/2002 | Stangel et al. |
| 2002/0016384 A1 | 2/2002 | Moszner et al. |
| 2003/0060536 A1 * | 3/2003 | Spange et al. ............... 523/116 |
| 2003/0087986 A1 | 5/2003 | Mitra |
| 2003/0108488 A1 | 6/2003 | Rajaiah |
| 2003/0152891 A1 * | 8/2003 | Chiu et al. ............... 433/215 |
| 2003/0166737 A1 | 9/2003 | Dede et al. |
| 2003/0166740 A1 | 9/2003 | Mitra et al. |
| 2003/0166816 A1 | 9/2003 | Bissinger et al. |
| 2003/0181541 A1 | 9/2003 | Wu et al. |
| 2003/0187092 A1 | 10/2003 | Fujiwara |
| 2003/0195273 A1 | 10/2003 | Mitra |
| 2003/0196914 A1 | 10/2003 | Tzou et al. |
| 2003/0198914 A1 * | 10/2003 | Brennan et al. ............... 433/9 |
| 2004/0067311 A1 * | 4/2004 | Baudin ............ C07C 69/63 427/301 |
| 2004/0110864 A1 | 6/2004 | Hecht et al. |
| 2004/0137409 A1 * | 7/2004 | Savic ............ A61C 13/0003 433/203.1 |
| 2004/0151691 A1 | 8/2004 | Oxman et al. |
| 2004/0192804 A1 * | 9/2004 | Kura et al. ............... 522/65 |
| 2004/0206932 A1 | 10/2004 | Abuelyaman |
| 2005/0074716 A1 | 4/2005 | Cleary et al. |
| 2005/0113477 A1 | 5/2005 | Oxman et al. |
| 2005/0133384 A1 | 6/2005 | Cinader |
| 2005/0154081 A1 | 7/2005 | Yin |
| 2005/0175965 A1 | 8/2005 | Craig et al. |
| 2005/0175966 A1 | 8/2005 | Falsafi et al. |
| 2005/0176844 A1 | 8/2005 | Aasen et al. |
| 2005/0252413 A1 | 11/2005 | Kangas et al. |
| 2005/0252414 A1 | 11/2005 | Craig et al. |
| 2005/0256223 A1 | 11/2005 | Kolb et al. |
| 2005/0277084 A1 | 12/2005 | Cinader et al. |
| 2006/0030637 A1 | 2/2006 | Mitra |
| 2006/0069181 A1 | 3/2006 | Thalacker |
| 2006/0084026 A1 | 4/2006 | Cinader et al. |
| 2006/0159645 A1 * | 7/2006 | Miller et al. ............... 424/70.12 |
| 2007/0039519 A1 | 2/2007 | Kangas et al. |
| 2007/0207094 A1 | 9/2007 | Oxman |
| 2007/0248927 A1 | 10/2007 | Luchterhandt |
| 2008/0096150 A1 | 4/2008 | Cinader |
| 2008/0299519 A1 * | 12/2008 | Craig et al. ............... 433/217.1 |
| 2009/0011388 A1 | 1/2009 | Craig |
| 2009/0030101 A1 | 1/2009 | Sang et al. |
| 2009/0075239 A1 | 3/2009 | Abuelyaman |

(56) References Cited

U.S. PATENT DOCUMENTS

FOREIGN PATENT DOCUMENTS

| | | |
|---|---|---|
| DE | 273 846 A1 | 11/1989 |
| DE | 199 18 974 A1 | 12/1999 |
| DE | 695 18 037 T2 | 3/2001 |
| EP | 0 115 410 | 8/1984 |
| EP | 0 115 812 A2 | 8/1984 |
| EP | 59-135272 | 8/1984 |
| EP | 60-089752 | 5/1985 |
| EP | 0 173 567 A2 | 3/1986 |
| EP | 61-151104 | 7/1986 |
| EP | 0 115 948 A1 | 10/1986 |
| EP | 0 201 031 A2 | 11/1986 |
| EP | 0 237 233 A2 | 9/1987 |
| EP | 0 201 778 B1 | 12/1988 |
| EP | 0 184 095 B1 | 7/1989 |
| EP | 323120 | 7/1989 |
| EP | 0 206 810 B1 | 4/1990 |
| EP | 0 335 645 B1 | 8/1992 |
| EP | 0 373 384 A1 | 10/1992 |
| EP | 0 537 774 A1 | 4/1993 |
| EP | 0 323 012 B1 | 5/1993 |
| EP | 0 351 076 B1 | 8/1993 |
| EP | 06-041162 | 2/1994 |
| EP | 0 509 516 B1 | 3/1997 |
| EP | 0 897 710 B1 | 2/1999 |
| EP | 0 661 034 A1 | 3/1999 |
| EP | 0 712 622 B1 | 9/1999 |
| EP | 1051961 | 11/2000 |
| EP | 1051961 B1 | 11/2000 |
| EP | 1121924 A2 | 8/2001 |
| EP | 1 141 094 B1 | 7/2002 |
| EP | 1 287 805 A1 | 3/2003 |
| EP | 1 346 717 A1 | 9/2003 |
| EP | 1 486 197 | 12/2004 |
| GB | 2 251 861 A | 7/1992 |
| JP | 59015468 | 1/1984 |
| JP | 10-512567 | 12/1998 |
| JP | 11139920 | 5/1999 |
| JP | 2000204010 | 7/2000 |
| JP | 2001072936 | 3/2001 |
| JP | 2004182661 | 7/2004 |
| WO | WO 1998/003443 | 1/1998 |
| WO | WO 98/46198 | 10/1998 |
| WO | WO 00/30591 | 6/2000 |
| WO | WO 00/38619 A2 | 7/2000 |
| WO | WO 00/38619 A3 | 7/2000 |
| WO | WO 00/42092 A1 | 7/2000 |
| WO | WO 01/07444 A1 | 2/2001 |
| WO | WO 01/30304 A1 | 5/2001 |
| WO | WO 01/30305 A1 | 5/2001 |
| WO | WO 01/30306 A1 | 5/2001 |
| WO | WO 01/30307 A1 | 5/2001 |
| WO | WO 0138449 | 5/2001 |
| WO | WO 01/92271 A1 | 12/2001 |
| WO | WO 02/02057 A1 | 1/2002 |
| WO | WO 02/11642 A1 | 2/2002 |
| WO | WO 02/092021 A1 | 11/2002 |
| WO | WO 2003/013444 A1 | 2/2003 |
| WO | WO 2003/063804 A1 | 8/2003 |
| WO | WO 2003/068174 A1 | 8/2003 |
| WO | WO 2005/004819 A | 1/2005 |
| WO | WO 2005/018581 A | 3/2005 |
| WO | WO 2006/014597 | 2/2006 |
| WO | WO 2006/020760 | 2/2006 |
| WO | WO 2007/075666 A1 | 7/2007 |

OTHER PUBLICATIONS

U.S. Appl. No. 60/494,603, filed Aug. 12, 2003, entitled "Dental Compositions and Methods".

U.S. Appl. No. 60/586,326, filed Jul. 8, 2004, entitled "Dental Methods, Compositions, and Kits Including Acid-sensitive Dyes".

U.S. Appl. No. 60/600,558, filed Aug. 11, 2004 entitled "Dental Methods, Compositions, and Kits Including Acid-sensitive Dyes".

Banerjee et al., *Ind. Eng. Chem. Res.*, vol. 35, No. 9, pp. 3100-3107 "Polymer Precipitation Using a Micellar Nonsolvent: The Role of Surfactant—Polymer Interactions and the Development of a Micro-encapsulation Technique", (1996).

Buonocore et al., *J. Dent. Res.*, vol. 35, No. 6, pp. 846-851, "A Report on a Resin Composition Capable of Bonding to Human Dentin Surfaces", (1956).

Floyd Green, The Sigma-Aldrich Handbook of Stains, Dyes, & Indicators [with/Transmission Spectrum Reference], Aldrich Chem. Co., Milwaukee, WI (1990).

Holmberg et al., "Microemulsions," Chapter 6, *Surfactants and Polymers in Aqueous Solution*, Second Edition, John Wiley & Sons, pp. 138-155 (2003; Reprinted with corrections in 2004).

ISO Standard 4049:2000.

ISO Standard 7489.

ISO Standard 9917-1:2003.

Leung et al., "Ch. 9, Microemulsions: Formation, Structure, Properties, and Novel Applications," *Surfactants in Chemical/Processing Engineering*, Marcel Dekker, Inc., New York and Basel, Title page, Publication page, and pp. 315-367(1988).

Ostrovosky et al., "Mechanism of Microemulsion Formation in Systems with Low Interfacial Tension: Occurence, Properties, and Behavior of Microemulsions," *Journal of Colloid and Interface Science*, 102(1): 206-226 (Nov. 1984).

Overbeek et al., "Microemulsions," in *Surfactants*, Th. F. Thadros, Ed., Academic Press, London, Title Page, Table of Contents, pp. 111-132 (1984).

Ruckenstein et al., "Stability of Microemulsions," *J. Chem. Soc. Faraday Trans* II, vol. 71; pp. 1690-1707 (1975).

Rumphorst, et al. "Examination of the Formulation of an Innovative Single-Component Bonding System," *Signature*, vol. 6, No. 1, pp. 1-3 (Sep. 2000).

Safran et al., "Phase Diagrams for Microemulsions," *Physical Review Letters*, vol. 50, No. 24, pp. 1930-1933 (Jun. 13, 1983).

Xu et al., *J. Phys. Chem.*, 97:11350-11353 (1993).

U.S. Appl. No. 60/600,658, filed Aug. 11, 2004, entitled "Self-adhesive Compositions Including a Plurality of Acidic Compounds".

Dyba et al., J. Chem. Soc., "1-Hydroxyalkane-1,1-diyldiphosphonates as potent chelating agents for metal ions. Potentiometric and spectroscopic studies of copper(II) coordination" Dalton Trans. (1996), 1119-1123.

Gumienna-Kontecka et al., J. Inorg. Biochem., Bisphosphonate chelating agents Coordination ability of 1-phenyl-1-hydroxymethylene bisphosphonate towards $Cu^{2+}$ ions, 89 (2002), 13-17.

Kieczykowski et al., J. Org. Chem., "Preparation of (4-Amino-1-Hydroxybutylidene) bisphosphonic Acid Sodium Salt, MK-217 (Alendronate Sodium). An Improved Procedure for the Preparation of 1-Hydroxy-1,1-bisphosphonic Acids," (1995), 60, 8310-8312.

Mathis et al., Dental Materials, "Properties of a New Glass Ionomer/Composite Resin Hybrid Restorative," Table of Contents, pp. 355-358.

Mathis et al., Journal of Dental Research, "Properties of a New Glass Ionomer/Composite Resin Hybrid Restorative," Abstract No. 51, vol. 66, pp. 113 (1987).

Moszner et al., Macromol. Chem. "Monomers for adhevise polymers, 2ᵃ, Synthesis and radical polymerisation of hydrolytically stable acrylic phosphonic acids" Phys. 200 (1999), 1062-67.

Technical Product Profile, "3M ESPE Adper™ Prompt™ L-Pop™ and Adper™ Prompt™ Self-Etch adhesives," Title page, Table of Contents, and pp. 3, 5-23, and Publication Page, 3M IPC (2002).

Tromelin et al., "Cetophosphonates ET Esters Cycliques D'Hydroxymethylenes Diphosphonates Syntheses, Structures ET Hydrolyse," Phosphorus Sufur Relat. Elem. 27, (1986), pp. 301-312.

Palma, R.G.; Turbino, M.L.; Watson, E.; Powers, J.M.: "Bond Strength to dentin with artificial carious lesions: influence of caries detecting dye" American Journal of Dentistry, vol. 11, No. 3, 1998, pp. 128-130, XP008055059 abstract.

(56) References Cited

OTHER PUBLICATIONS

Kazemi, R.B.; Meiers, J.C.; Peppers, K: "Effect of caries desclosing agents on bond strengths of total-etch and self-etching primer dentin bonding systems to resin composite" Operative Dentistry, vol. 27, No. 3, 2002, pp. 238-242, XP008054961, whole document.
TYRIAN™ SPE Universal Self-Priming Etchant, TYRIAN SPE General Information, BISCO, Inc., Schaumburg, IL [retrieved from the internet on Jul. 7, 2004] URL http://www.bisco.com/instructions/tyrianspe_instr_print.asp 8 pages.
S.J. Hodges et al., "Unusual Indelible Enamel Staining Following Fixed Appliance Treatment", 2000, pp. 303-306, vol. 27, copyright 2000 British Orthodontic Society.
Written Opinion of ISR for PCT/US2005/02491.
Written Opinion of ISR for PCT/US2004/025936.
IPER for PCT/US03/31387.
Written Opinion of ISR for PCT/US2005/028536.
Alberti, "Cationic Dyes for Acrylic Fibers IV. Catonic Dyes from 6-Methyl-2-(p-Aminophenyl) Benzothiazole and Angular 2-Aminonapthtothiazoles", Chimica e L'Industria, 1974, vol. 56, No. 10, pp. 684-686.
Billmeyer, Principles of Color Technology, Second Edition, New York, NY (1981).
"Blue No. 403", [online], [retrieved from the internet on Aug. 24, 2006], <http://www02.so-net.ne.jp/~tombo/ci/b403e.htm>, 1 page.
Clinpro Sealant, Technical Product Profile, No. 70-2009-2265-9, 3M ESPE, (2001), pp. 1-20.
"Color Center, Color Handbook, Anthrapyrimidine", Special Chem Innovations and Solutions [on line], [retrieved from the internet on Aug. 24, 2006], <http://www.specialchem4coatings.com/tc/color-handbook>, 2 pages.
"Colour Index", The Society of Dyers and Colourists [on line], [retrieved from the internet on Nov. 29, 2005], <http://www.sdc.org.uk/publications/ci4classes.htm>, 2 pages.
"Disperse Dyes", Technology Information Forecasting and Assessment Council, Asian and Pacific Centre for Transfer of Technology, [on line], [retrieved from the internet on Nov. 28, 2005], <http://www.tifac.org.in/offer/tsw/apctt10.htm>, 4 pages.
"Dye Classes for Principal Applications," Dr. Klaus Hunger (author and editor), Wiley Interscience Online Book, [retrieved from the internet on Nov. 29, 2005], <http://www.3.interscience.wiley.com/cgi-bin/summary/107642439/SUMMARY>, 3 pages.
"Epochem Products 2004", Epochem Co., Ltd, <http://www.Epochem.com>, 2002-2004, pp. 1-25.
"Essay: Dyes and Dyeing", Supplement to Experiment 9, Univ. of CO, Boulder, Dept. of Chem. and Biochem. 2006, pp. 63-70.
Freeman, "Synthetic Dyes Based on Toxicological Considerations", National Textile Center Annual Report, Sep. 1993, pp. 167-176.
Green, The Sigma-Aldrich Handbook of Stains, Dyes, and Indicators, Aldrich Chemical Company, pp. 284, 290, 291, 398, 647, 660, (1990).
Heitzman, "Organic Yellows for Plastics", Sun Chemical Corporation, Performance Plastics Business Unit, pp. 12-15.
"ONE-UP Bond F" literature, Tokuyama Corp., Product description and general information, 1 page, [date unknown but believed to be prior to the date of the filing of the present application].
Patel, "Synthesis of Monoazo Disperse Dyes from 2-Amino-4-Methylbenzothiazole and Their Application on Polyester Fiber", Oriental Journal Chemistry, 1996, vol. 12, No. 2, pp. 193-195.
StainsFile, "Anthraquinone Dyes", [retrieved from the internet on Nov. 28, 2005], <http://stasfile.info.StainsFile/dyes/class/clsanthq.htm>, 1 page.
The Complete Technology Book on Dyes & Dye Intermediates, National Institute of Industrial Research [on line], [retrieved from the internet on Nov. 29, 2005], <http://www.niir.org>, pp. 1-42. [ISBN: 81-86623-79-5].
Twenty-first Report of the Interagency Testing Committee to the Administrator; Receipt of Report and Request for Comments Regarding Priority List of Chemicals, Notices, Federal Register, vol. 52, No. 224, Nov. 1987, pp. 44830-44837.
International Search Report for Int'l Appln. No. PCT/US2003/041487, 3 pages.
International Search Report for Int'l Appln. No. PCT/US2004/025936, 3 pages.
International Search Report for Int'l Appln. No. PCT/US2005/024291, 4 pages.
International Search Report for Int'l Appln. No. PCT/US2005/028536, 4 pages.
International Search Report for Int'l Appln. No. PCT/US2007/087192, 3 pages.
Grant & Hackh's Chemical Dictionary, $5_{th}$ edition, (1987), pp. 197.

\* cited by examiner

METHODS OF USING A DENTAL COMPOSITION HAVING AN ACIDIC COMPONENT AND A PHOTOBLEACHABLE DYE

CROSS REFERENCE TO RELATED APPLICATIONS

This application is a national stage filing under 35 U.S.C. 371 of PCT/US2007/087192, filed Dec. 7, 2007, which claims priority to U.S. Application No. 60/869,741, filed Dec. 13, 2006, the disclosure of which is incorporated by reference in its/their entirety herein.

BACKGROUND

Color-changing dental compositions can be advantageous for use in a wide variety of dental and orthodontic applications. For example, a hardenable dental composition having an initial color that provides a visible contrast to the color of the tooth structure can aid the practitioner in properly placing or identifying the hardenable composition, after which the color preferably changes to colorless or tooth color to minimize visibility of the composition. Examples of such color-changing dental compositions include dental sealants, in which the initial color can aid the practitioner in accurately placing the composition in and/or on desired pits and fissures. Additional examples of such color-changing dental compositions include adhesives (e.g., dental and orthodontic adhesives), in which the initial color can aid the practitioner in removing excess or unwanted adhesive from the tooth structure.

Certain color-changing, hardenable dental compositions (preferably light-curable dental compositions) that include a photobleachable dye have found use in a variety of dental and orthodontic applications. For example, the photobleachable dye can impart an initial color to the composition to aid in placement of the composition in and/or on the desired areas of the tooth structure. After the practitioner determines that the hardenable dental composition has been properly placed or removed, exposure to actinic radiation (e.g., to harden a light-curable composition) can cause loss of color of the photobleachable dye (i.e., bleaching), thus minimizing visibility of the hardened dental composition.

Self-etching dental compositions are finding increasing utility in the dental and orthodontic areas. However, there exists a need for self-etching dental compositions that have useful color-changing properties.

SUMMARY

Self-etching dental compositions generally include an acidic component, typically having an acidic functionality including, but not limited to, one or more of phosphoric acid functionality, phosphonic acid functionality, and/or sulfonic acid functionality. It has now been found that the addition to self-etching dental compositions of photobleachable dyes that are typically used in conventional (i.e., not self-etching), color-changing dental compositions, results in dental compositions in which the expected color-changing properties suffer, for example, from poor initial color stability and/or undesirable color return after bleaching. It has now been found that certain photobleachable dyes can provide useful self-etching, color-changing dental compositions having adequate initial color stability and limited color return after bleaching.

In certain embodiments, the present invention provides methods of using a hardenable dental composition having an acidic component and a photobleachable dye. The hardenable dental composition includes: a hardenable component; an initiator for initiating hardening of the hardenable dental composition; an acidic component (preferably having phosphoric acid functionality, phosphonic acid functionality, and/or sulfonic acid functionality) having a $pK_a$ of less than 4.5 (and in certain embodiments less than 4 or even less than 3); and a photobleachable dye selected from the group consisting of aminoanthraquinone dyes, azo dyes, and combinations thereof. Preferably, the hardenable dental composition is self-etching.

In one embodiment, the present invention provides a method for treating an oral surface. The method includes: applying to the oral surface (e.g., a wet or dry tooth structure) a hardenable dental composition having an acidic component and a photobleachable dye as disclosed herein; hardening the hardenable dental composition; and observing the color of the hardened dental composition immediately after hardening and observing the aged color of the hardened dental composition after aging for at least 3 days at or neat body temperature (e.g., 37° C.) after hardening to determine that the aged color is substantially the same as the color immediately after hardening. In some embodiments, the hardenable dental composition has an initial color prior to hardening, and a final color after hardening, wherein the final color is different than the initial color.

In another embodiment, the present invention provides a method for bonding (e.g., using either direct or indirect methods) an orthodontic appliance to a tooth structure. The method includes: providing an orthodontic appliance having a base for bonding the appliance to the tooth structure; providing a hardenable dental composition including an acidic component and a photobleachable dye as described herein; contacting the hardenable dental composition with the tooth structure and the base of the orthodontic appliance; hardening the hardenable dental composition; and observing the color of the hardened dental composition immediately after hardening and observing the aged color of the hardened dental composition after aging for at least 3 days at or near body temperature after hardening to determine that the aged color is substantially the same as the color immediately after hardening. Optionally, the base of the orthodontic appliance can be a custom base for indirect bonding. A wide variety of methods can be used for applying the hardenable dental composition to the tooth structure (e.g., manually or using a transfer apparatus as described, for example, in U.S. Pat. No. 7,186,950 (Cinader et al.), or to the base of the orthodontic appliance (e.g., manually or using one or more of the assemblies described, for example, in U.S. patent application Ser. Nos. 11/425,461 and 11/425,457, both filed Jun. 21, 2006). Optionally, the base of the orthodontic appliance can have the hardenable dental composition thereon, in which case the appliance can preferably be provided as a precoated appliance.

In certain preferred embodiments, the present invention provides a method for treating a tooth structure that includes applying to the tooth structure (e.g., a wet or dry tooth structure) a hardenable dental composition that has an initial color prior to exposure to actinic radiation and includes: an ethylenically unsaturated compound with acid functionality and having a $pK_a$ of less than 4.5; an ethylenically unsaturated compound without acid functionality; a hardener for initiating hardening of the hardenable dental composition; and a photobleachable dye selected from the group consisting of aminoanthraquinone dyes, azo dyes, and combinations thereof; irradiating the hardenable dental composition to provide a hardened dental composition having a final color, the final color being different than the initial color; and observing the aged color of the hardened dental composition after aging for at least 3 days at or near body temperature (e.g., 37° C.) after hardening to determine that the aged color is substantially the same as the final color. Preferably, the hardened dental composition adheres to the tooth structure (e.g., uncut enamel, dentin, and/or cementum) with an adhesion value of at least 6 MPa using a test method as described herein (e.g., Test Method B). Optionally, the method further includes bonding an orthodontic appliance to the hardened and/or hardenable dental composition, which preferably is applied to at least a portion of a surface (e.g., a labial or lingual surface) of the tooth structure.

DEFINITIONS

As used herein, "dental composition" refers to an unfilled or filled (e.g. a composite) material (e.g., a dental or orthodontic material) capable of adhering (e.g., bonding) to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives (e.g., a restorative filling material), liners, sealants (e.g., orthodontic sealants), and coatings. Oftentimes a dental composition can be used to bond a dental article to a tooth structure.

As used herein, a "self-etching" composition refers to a composition that bonds to a dental structure surface without pretreating the dental structure surface with an etchant. Preferably, a self-etching composition can also function as a self-primer wherein no separate etchant or primer is used.

As used herein, a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

As used herein, "dental article" refers to an article that can be adhered (e.g., bonded) to an oral surface (e.g., a tooth structure). Dental articles include, for example, crowns, bridges. veneers, inlays, onlays, fillings, orthodontic appliances and devices, prostheses (e.g., partial or full dentures), bite blocks, and aligner retention structures (e.g., as described in U.S. Pat. No. 6,830,450 (Knopp et al.)).

As used herein, "orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e., single or multi-layer adhesives). Optionally, the orthodontic appliance can include, bonded to the base thereof, a compressible material (e.g., a porous material having a hardenable dental composition at least partially within the pores thereof as described, for example, in U.S. patent application Ser. No. 11/551,823, filed Oct. 22, 2006).

As used herein, an "oral surface" refers to a soft or hard surface in the oral environment. Hard surfaces typically include tooth structure including, for example, natural and artificial tooth surfaces, bone, tooth models, dentin, enamel, cementum, and the like.

As used herein, a "wet" tooth structure surface refers to a surface of a tooth structure upon which an aqueous liquid (e.g., water or saliva) is present and visible to the naked human eye.

As used herein, a "dry" tooth structure surface refers to a surface of a tooth structure that has been dried (e.g., air dried) and does not have present visible water.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

As used herein, "hardened" refers to a material or composition that has been cured (e.g., polymerized or crosslinked) or solidified.

As used herein, "hardener" refers to something that initiates hardening of a resin. A hardener may include, for example, a polymerization initiator system, a photoinitiator system, and/or a redox initiator system.

As used herein, "photobleachable" refers to loss of color upon exposure to actinic radiation. As used herein, "actinic" radiation refers to light emitted in the ultraviolet (UV) and/or visible portion of the electromagnetic spectrum typically having a wavelength of 250 to 800 nanometers (nm). Methods as disclosed herein preferably include exposure to visible light having a wavelength of 400 to 800 nm.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

In certain embodiments, the present invention provides methods of using a hardenable dental composition having an acidic component and a photobleachable dye. The hardenable dental composition includes: a hardenable component; an initiator for initiating hardening of the hardenable dental composition; an acidic component (preferably having phosphoric acid functionality, phosphonic acid functionality, and/or sulfonic acid functionality) having a $pK_a$ of less than 4.5 (and in certain embodiments less than 4 or even less than 3); and a photobleachable dye selected from the group consisting of aminoanthraquinone dyes, azo dyes, and combinations thereof. Preferably, the hardenable dental composition is self-etching.

Dental compositions useful in methods of the present invention preferably undergo a color change from an initial color to a final color upon exposing the composition to a source of actinic radiation for a sufficient time to effect color change in the composition. The initial and final colors are different from each other. Preferably, the initial color is one that is easily detected by the unaided human eye to confirm proper placement of the composition on the oral surface. As used herein, "initial color" refers to the color of the hardenable dental composition, preferably after being applied to the oral surface, but prior to exposure to actinic radiation. As used herein, "final color" refers to the color of the hardened dental composition immediately, e.g., at most 1 hour, preferably at most 15 minutes, more preferably at most 5 minutes, and sometimes at most 1 minute of even less (e.g., 15 seconds or less) after hardening.

It is also preferred that the final color have a naturally occurring dentition shade so as to closely match the surrounding environment or be sufficiently clear so as to transmit the color of the underlying dentition. A "naturally occurring dentition shade" can be one that corresponds to the well known alpha-numeric VITA-shade color designation system or other shade system for characterizing dentition shades. In certain embodiments, the final color is able to transmit the color of an underlying surface.

More quantitatively, the change in color from the initial color to a final color is preferably quantified by a colorimetry test as described in the Test Methods Section below. Using the Color Test, a value of $\Delta E^*$ is determined, which indicates the total color change in a 3-dimensional color space. The human eye can detect a color change of approximately 3 $\Delta E^*$ units in normal lighting conditions. Dental compositions as disclosed herein are preferably capable of having a color change, $\Delta E^*$, of greater than 10; more preferably, $\Delta E^*$ is greater than 15; most preferably $\Delta E^*$ is greater than 20.

The color change in the dental composition can be initiated by light. Preferably, the color change is initiated by actinic radiation using, for example, a dental curing light that emits visible light for a sufficient amount of time. The mechanism that initiates the color change in the dental compositions may be separate from or substantially simultaneous with the hardening mechanism that hardens the hardenable dental composition. For example, a hardenable dental composition may harden when polymerization is initiated chemically (e.g., redox initiation) or thermally, and the color change from an initial color to a final color may occur subsequent to the hardening process upon exposure to actinic radiation.

The aged color of the hardened dental composition is observed after aging for at least 3 days at or near body temperature (e.g., 37° C.) after hardening to determine that the aged color is substantially the same as the final color. As used herein, "substantially the same" color means that no change in color is detected by the human eye under normal lighting conditions. More quantitatively, the change in color from the final color to the aged color is preferably quantified by a colorimetry test as described in the Test Methods Section below. Using the Color Test, a value of $\Delta E^*$ is determined, which indicates the total color change in a 3-dimensional color space. A color change of 3 $\Delta E^*$ units or less in normal lighting conditions is considered to be substantially the same color.

Accordingly, observing color and color changes can be performed by the human eye, preferably under normal lighting conditions. Alternatively, observing color and color changes can be detected and quantified by a colorimetry test as described in the Test Methods Section below.

Photobleachable Dyes

Photobleachable dyes suitable for use in methods of the present invention include dyes selected from the group consisting of aminoanthraquinone dyes, azo dyes, and combinations thereof. The use of aminoanthraquinone and/or azo dyes in hardenable dental compositions including an acidic component with a pKa of less than 4.5 has been found to overcome at least some of the problems observed with other photobleachable dyes including, for example, poor initial color stability and/or undesirable color return after bleaching.

As used herein, the term "aminoanthraquinone dye" refers to a dye that includes, but is not limited to, an aminoanthraquinone group (i.e., at least one amino group directly attached to an anthraquinone ring carbon). Each amino group can independently be a primary amine (i.e., —$NH_2$), a secondary amine (i.e., —NHR), or a tertiary amine (i.e., —$NR^2R^3$), wherein R, $R^2$, and $R^3$ each independently represent an organic group. Useful aminoanthraquinone dyes include, for example, mono-, di-, tri-, and tetra-aminoanthraquinone dyes. Preferred aminoanthraquinone dyes include, for example, 2-aminoanthraquinone dyes, 1,4-diaminoanthraquinone dyes, 1,5-diaminoanthraquinone dyes, 1,8-diaminoanthraquinone dyes, 1,4,5-triaminoanthraquinone dyes, and 1,4,5,8-tetraminoanthraquinone dyes.

A preferred class of photobleachable diaminoanthraquinone dyes includes 1,4-diaminoanthraquinone dyes of the formula (Formula I):

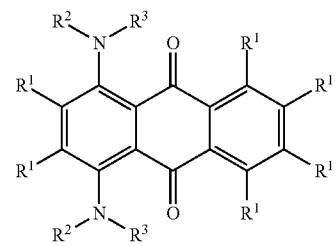

wherein each $R^1$, $R^2$, and $R^3$ is independently hydrogen or an organic group. In certain embodiments, each $R^1$ and each $R^2$ is hydrogen, and each $R^3$ is an organic group (and preferably an organic moiety).

Dyes of the formula (Formula I) include, for example, those available under the trade designations REACTINT Blue Dye X17AB from Millikin Research Corp., Spartanburg, S.C. (an aminoanthraquinone compound based on NMR spectroscopic analysis); REACTINT Black Dye X95AB from Millikin Research Corp., Spartanburg, S.C. (a blend of monoazo and aminoanthraquinone compounds based on NMR spectroscopic analysis); Solvent Blue 35 from Sigma-Aldrich (i.e., 1,4-Bis(butylamino)-9,10-anthracenedione; see also "The Sigma-Aldrich Handbook of Stains, Dyes and Indicators," Floyd J. Green, Aldrich Chemical Company, 1990, p. 647); Disperse Blue 3 from Sigma-Aldrich (Celliton Fast Blue FFR; an aminoanthraquinone dye prepared by condensing methylamine and ethanolamine with quinizarin and leucoquinizarin in isobutanol, and oxidizing the condensation product; see also "The Sigma-Aldrich Handbook of Stains, Dyes and Indicators," Floyd J. Green, Aldrich Chemical Company, 1990, p. 284); and combinations thereof.

As used herein, the term "azo" dye refers to a dye that includes, but is not limited to, an azo (i.e., —N=N—) group. Thus, typical azo dyes are of the formula R—N=N—R, wherein each R independently represents an organic group (and preferably an organic moiety). Azo dyes include those having one azo group (i.e., a monoazo dye), two azo groups (i.e., a disazo or bisazo dye), or even more azo groups.

A preferred class of photobleachable azo dyes includes those of the formula $Ar^1$—N=N—$Ar^2$, wherein each $Ar^1$ and $Ar^2$ independently represents an aryl group or a heteroaryl group. $Ar^1$ and $Ar^2$ can be the same or different.

Suitable monoazo dyes of the formula $Ar^1$—N=N—$Ar^2$ include, for example, those available under the trade designations REACTINT Red Dye X64 from Millikin Research Corp., Spartanburg, S.C. (a monoazo compound based on NMR spectroscopic analysis); REACTINT Black Dye X95AB from Millikin Research Corp., Spartanburg, S.C. (a blend of monoazo and aminoanthraquinone compounds based on NMR spectroscopic analysis); Disperse Red 1 from Sigma-Aldrich (Celliton Scarlet B; a red monoazo dye prepared by coupling diazotized 4-nitroaniline to 2-(N-ethylanilino)ethanol; see also "The Sigma-Aldrich Handbook of Stains, Dyes and Indicators," Floyd J. Green, Aldrich Chemical Company, 1990, p. 290); Disperse Red 13 from Sigma-Aldrich (Celliton Fast Ruby B; a monoazo dye prepared by coupling diazotized 2-chloro-4-nitroaniline to 2-(N-ethylanilino)ethanol; see also "The Sigma-Aldrich Handbook of Stains, Dyes and Indicators," Floyd J. Green, Aldrich Chemical Company, 1990, p. 291); Calconcarboxylic Acid from Sigma-Aldrich (3-hydroxy-4-(2-hydroxy-4-sulfo-1-naphthylazo)naphthalene-2-carboxylic acid; prepared by coupling diazotized 1-amino-2-naphthol-4-sulfonic acid to 3-hydroxy-2-naphthoic acid; see also "The Sigma-Aldrich Handbook of Stains, Dyes and Indicators," Floyd J. Green, Aldrich Chemical Company, 1990, p. 398); and combinations thereof.

Suitable disazo dyes of the formula $Ar^1$—N=N—$Ar^2$ include, for example, Sudan Black B from Sigma-Aldrich (Fat Black HB, Solvent Black 3; a neutral disazo dye prepared by first coupling diazotized aniline to 1-napthylamine to form an intermediate, then diazotizing the intermediate and coupling the resulting product to 2,3-dihydro-2,2-dimethylperimidine; see also "The Sigma-Aldrich Handbook of Stains, Dyes and Indicators," Floyd J. Green, Aldrich Chemical Company, 1990, p. 660); and combinations thereof.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable groups are those that do not interfere with the hardening or the color-changing properties of the composition. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" (e.g., "organic group" and "organic moiety") are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, amino, carboxyl, etc. Thus, "alkyl group" includes ether groups, haloalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Bleaching properties of the photobleachable dyes can be readily determined by irradiating the dental composition having the acidic component and the photobleachable dye therein, and evaluating the change in color as described herein. Preferably, at least one photobleachable dye is at least partially soluble in the hardenable resin.

Hardenable dental compositions for use in methods of the present invention typically include at least 0.001% by weight photobleachable dye, and more preferably at least about 0.01% by weight photobleachable dye, based on the total weight of the hardenable dental composition. The hardenable dental composition preferably includes at most about 1% by weight photobleachable dye, and more preferably at most about 0.1% by weight photobleachable dye, based on the total weight of the hardenable dental composition. The amount of photobleachable dye can vary depending on its extinction coefficient, the ability of the human eye to discern the initial color, and the desired color change.

Acidic Components

Hardenable dental compositions used in methods of the present invention include an acidic component having a $pK_a$ of less than 4.5, and in certain embodiments less than 4 or even less than 3. The acidic component can be an inorganic acid (e.g., hydrochloric acid, hydrobromic acid, and/or nitric acid) or an organic acid (e.g., a monomeric, an oligomeric, and/or a polymeric acid) including, for example, one or more oxyacids of carbon, sulfur, and/or phosphorus. The organic acid can be polymerizable or non-polymerizable.

Hardenable dental compositions can include any of a wide variety of monomeric organic acids such as formic acid, trifluoroacetic acid, trichloroacetic acid, dichloroacetic acid, chloroacetic acid, tribromoacetic acid, dibromoacetic acid, bromoacetic acid, acetic acid, α-chloropropionic acid, propionic acid, maleic acid, fumeric acid, citraconic acid, pivalic acid, methacrylic acid, acrylic acid, trihydroxybenzoic acid, benzoic acid, camphorquinonesulfonic acid, camphorsulfonic acid, toluenesulfonic acid, trifluoromethanesulfonic acid, benzenesulfonic acid, 2-hydroxy-4-methoxybenzophenone-5-sulfonic acid, 2-acrylamido-2-methylpropane sulfonic acid, 2-naphthalene sulfonic acid, para-nitrophenol, 2,4-dinitrophenol, phenol, and combinations thereof.

Oligomeric and/or polymeric organic acids include, for example, polyalkenoic acids that are commonly used to prepare glass ionomer cements, and those described, for example, in U.S. Pat. No. 3,655,605 (Smith); U.S. Pat. No. 4,016,124 (Crisp et al.); U.S. Pat. No. 4,089,830 (Tezuka et al.); U.S. Pat. No. 4,143,018 (Crisp et al.); U.S. Pat. No. 4,342,677 (Muramatsu et al.); U.S. Pat. No. 4,360,605 (Schmitt et al.), and U.S. Pat. No. 4,376,835 (Schmitt et al.). Exemplary oligomeric and/or polymeric organic acids include, but are not limited to, carboxylic acid functional polymers (e.g., homopolymers and/or copolymers) of unsaturated mono-, di- and/or tricarboxylic acids and/or their anhydrides, and can optionally be substituted with one or more ethylenically unsaturated groups. Such oligomeric and/or polymeric organic acids include, for example, homopolymers of poly(meth)acrylic acid; copolymers of (meth)acrylic and itaconic acid; copolymers of (meth) acrylic and maleic acid; copolymers of methyl vinyl ether and maleic anhydride or maleic acid; copolymers of ethylene and maleic anhydride or maleic acid; and copolymers of styrene and maleic anhydride or maleic acid; each of which can optionally be substituted with one or more polymerizable ethylenically unsaturated groups. In certain embodiments, preferred oligomeric and/or polymeric acids include (meth)acrylate functionalized copolymers of acrylic acid, (meth)acrylic acid, maleic acid, and itaconic acid as described, for example, in EP 0 323 120 B1 (Mitra). Mixtures of oligomeric and/or polymeric organic acids can be used if desired. A wide variety of polymerizable organic acids (e.g., acidic hardenable components) are further described hereinafter.

Typically, the acidic component includes phosphoric acid functionality, phosphonic acid functionality, sulfonic acid functionality, or combinations thereof. In addition to such an acidic component, the hardenable dental composition can also include other acidic components such as acidic components having carboxylic acid functionality (e.g., citric acid dimethacrylate, CDMA). The acidic component can be the same or different than acidic hardenable components further described herein.

Exemplary acidic components having a $pK_a$ of less than 4.5 include, for example, glycerol dimethacrylate phosphate (GDMA-P), 6-methacryloxyhexyl phosphate (MHP), bis (methacryloxyethyl)phosphate (available under the trade designation KAYAMER PM-2 from Nippon Kayaku, Japan), 10-methacryloxydecyl phosphate, and combinations thereof.

Dental Compositions

Dental compositions used in methods of the present invention include a hardener. In certain embodiments, the hardener includes a sensitizing compound (e.g., a photosensitizer). Preferably the sensitizing compound is different than the photobleachable dye. In certain embodiments, the hardener further includes an electron donor and an iodonium salt.

Optionally, hardenable dental compositions as described herein can further include, for example, an initiator system, an ethylenically unsaturated compound, and/or one or more fillers. Hardenable and hardened dental compositions as described herein can be used for a variety of dental and orthodontic applications that utilize a material capable of adhering (e.g., bonding) to a tooth structure. Uses for such hardenable and hardened dental compositions include, for example, uses as adhesives (e.g., dental and/or orthodontic adhesives), cements (e.g., glass ionomer cements, resin-modified glass ionomer cements, and orthodontic cements), primers (e.g., orthodontic primers), restoratives, liners, sealants (e.g., orthodontic sealants), coatings, and combinations thereof. Such hardenable dental compositions can be applied to a tooth structure by a wide variety of methods. For example, a sealant can be applied to the tooth structure manually (e.g., using a brush or syringe) or by using a tray (e.g., an impression tray).

Hardenable compositions (e.g., hardenable dental compositions) as described herein typically include a hardenable (e.g., polymerizable) component, thereby forming hardenable (e.g., polymerizable) compositions. The hardenable component can include a wide variety of chemistries, such as ethylenically unsaturated compounds (with or without acid functionality), epoxy (oxirane) resins, vinyl ethers, photopolymerization systems, redox cure systems, glass ionomer cements, polyethers, polysiloxanes, and the like. In some embodiments, the compositions can be hardened (e.g., polymerized by conventional photopolymerization and/or chemical polymerization techniques) prior to applying the hardened dental composition. In other embodiments, a dental composition can be hardened (e.g., polymerized by conventional photopolymerization and/or chemical polymerization techniques) after applying the dental composition.

In certain embodiments, the compositions are photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements (e.g., conventional and resin-modified glass ionomer cements), redox cure systems, and combinations thereof.

Suitable photopolymerizable components that can be used in the dental compositions as disclosed herein include, for example, epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional acrylates, epoxy-functional methacrylates, and combinations thereof.

Ethylenically Unsaturated Compounds

Dental compositions as disclosed herein may include one or more hardenable components in the form of ethylenically unsaturated compounds with or without acid functionality, thereby forming hardenable compositions.

Suitable hardenable compositions may include hardenable components (e.g., photopolymerizable compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

The compositions (e.g., photopolymerizable compositions) may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The hardenable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments hardenable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the hardenable components can be used if desired.

Preferably, dental compositions as disclosed herein include at least 5% by weight, more preferably at least 10% by weight, and most preferably at least 15% by weight ethylenically unsaturated compounds, based on the total weight of the unfilled composition. Preferably, dental compositions as disclosed herein include at most 95% by weight, more preferably at most 90% by weight, and most preferably at most 80% by weight ethylenically unsaturated compounds, based on the total weight of the unfilled composition.

Preferably, dental compositions as disclosed herein include ethylenically unsaturated compounds without acid functionality. Preferably, dental compositions as disclosed herein include at least 5% by weight (wt-%), more preferably at least 10% by weight, and most preferably at least 15% by weight ethylenically unsaturated compounds without acid functionality, based on the total weight of the unfilled composition. Preferably, dental compositions as disclosed herein include at most 95% by weight, more preferably at most 90% by weight, and most preferably at most 80% by weight ethylenically unsaturated compounds without acid functionality, based on the total weight of the unfilled composition.

Ethylenically Unsaturated Compounds with Acid Functionality

Dental compositions as disclosed herein may include one or more hardenable components in the form of ethylenically unsaturated compounds with acid functionality, thereby forming hardenable compositions.

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain compositions for use in preferred methods of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Pat. Application Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP U.S. Pat. No. 1,051,961 (Kuraray Co., Ltd.).

Dental compositions as disclosed herein can also include compositions that include combinations of ethylenically unsaturated compounds with acid functionality. Preferably the compositions are self-adhesive and are non-aqueous. For example, such compositions can include: a first compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C1-C4 hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a C5-C12 hydrocarbon group; an ethylenically unsaturated compound without acid functionality; an initiator system; and a filler. Such compositions are described, for example, in U.S. Patent Application Publication No. 2007/0248927 A1 (Luchterhandt et al.).

Preferably, dental compositions as disclosed herein include at least 1% by weight, more preferably at least 3% by weight, and most preferably at least 5% by weight ethylenically unsaturated compounds with acid functionality, based on the total weight of the unfilled composition. Preferably, dental compositions as disclosed herein include at most 80% by weight, more preferably at most 70% by weight, and most preferably at most 60% by weight ethylenically unsaturated compounds with acid functionality, based on the total weight of the unfilled composition.

Glass Ionomers

Hardenable compositions as described herein may include glass ionomer cements such as conventional glass ionomer cements that typically employ as their main ingredients a homopolymer or copolymer of an ethylenically unsaturated carboxylic acid (e.g., poly acrylic acid, copoly (acrylic, itaconic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass.

The glass ionomer cements may also include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Ionomer/Composite Resin Hybrid Restorative", Abstract No. 51, J. Dent Res., 66:113 (1987) and as in U.S. Pat. No. 5,063,257 (Akahane et al.), U.S. Pat. No. 5,520,725 (Kato et al.), U.S. Pat. No. 5,859,089 (Qian), U.S. Pat. No. 5,925,715 (Mitra) and U.S. Pat. No. 5,962,550 (Akahane et al.). In another type of RMGI, the cement may include a polycarboxylic acid, an acrylate or methacrylate-functional monomer, and a redox or other chemical cure system, e.g., as described in U.S. Pat. No. 5,154,762 (Mitra et al.), U.S. Pat. No. 5,520,725 (Kato et al.), and U.S. Pat. No. 5,871,360 (Kato). In another type of RMGI, the cement may include various monomer-containing or resin-containing components as described in U.S. Pat. No. 4,872,936 (Engelbrecht), U.S. Pat. No. 5,227,413 (Mitra), U.S. Pat. No. 5,367,002 (Huang et al.), and U.S. Pat. No. 5,965,632 (Orlowski). RMGI cements are preferably formulated as powder/liquid or paste/paste systems, and contain water as mixed and applied. The compositions are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Pat. No. 6,765,038 (Mitra).

Photoinitiator Systems

In certain embodiments, the compositions of the present invention are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Suitable photoinitiators for polymerizing cationically photopolymerizable compositions include binary and tertiary systems. Typical tertiary photoinitiators include an iodonium salt, a photosensitizer, and an electron donor compound as described in EP 0 897 710 (Weinmann et al.); and in U.S. Pat. No. 5,856,373 (Kaisaki et al.), U.S. Pat. No. 6,084,004 (Weinmann et al.), U.S. Pat. No. 6,187,833 (Oxman et al.), U.S. Pat. No. 6,187,836 (Oxman et al.), and U.S. Pat. No. 6,765,036 (Dede et al.). The compositions of the invention can include one or more anthracene-based compounds as electron donors. In some embodiments, the compositions include multiple substituted anthracene compounds or a combination of a substituted anthracene compound with unsubstituted anthracene. The combination of these mixed-anthracene electron donors as part of a photoinitiator system provides significantly enhanced cure depth and cure speed and temperature insensitivity when compared to comparable single-donor photoinitiator systems in the same matrix. Such compositions with anthracene-based electron donors are described in U.S. Pat. Application Publication No. 2005/0113477 A1 (Oxman et al.).

Suitable iodonium salts include tolylcumyliodonium tetrakis(pentafluorophenyl)borate, tolylcumyliodonium tetrakis(3,5-bis(trifluoromethyl)-phenyl)borate, and the diaryl iodonium salts, e.g., diphenyliodonium chloride, diphenyliodonium hexafluorophosphate, diphenyliodonium hexafluoroantimonate, and diphenyliodonium tetrafluoroborate. Suitable photosensitizers are monoketones and diketones that absorb some light within a range of 450 nm to 520 nm (preferably, 450 nm to 500 nm). More suitable compounds are alpha diketones that have some light absorption within a range of 450 nm to 520 nm (even more preferably, 450 nm to 500 nm). Preferred compounds are camphorquinone, benzil, furil, 3,3,6,6-tetramethylcyclohexanedione, phenanthraquinone and other cyclic alpha diketones. Most preferred is camphorquinone. Suitable electron donor compounds include substituted amines, e.g., ethyl 4-(dimethylamino)benzoate and 2-butoxyethyl 4-(dimethylamino)benzoate; and polycondensed aromatic compounds (e.g. anthracene).

The initiator system is present in an amount sufficient to provide the desired rate of hardening (e.g., polymerizing and/or crosslinking). For a photoinitiator, this amount will be dependent in part on the light source, the thickness of the layer to be exposed to radiant energy, and the extinction coefficient of the photoinitiator. Preferably, the initiator system is present in a total amount of at least 0.01 wt-%, more preferably, at least 0.03 wt-%, and most preferably, at least 0.05 wt-%, based on the weight of the composition. Preferably, the initiator system is present in a total amount of no more than 10 wt-%, more preferably, no more than 5 wt-%, and most preferably, no more than 2.5 wt-%, based on the weight of the composition.

Redox Initiator Systems

In certain embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions and may include glass ionomer cements, resin-modified glass ionomer cements, redox cure systems, and combinations thereof.

The chemically hardenable compositions may include redox cure systems that include a hardenable component (e.g., an ethylenically unsaturated polymerizable component) and redox agents that include an oxidizing agent and a reducing agent. Suitable hardenable components, redox agents, optional acid-functional components, and optional fillers that are useful in the present invention are described in U.S. Pat. No. 6,982,288 (Mitra et al.) and U.S. Pat. No. 7,173,074 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light.

The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the hardenable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. No. 6,982,288 (Mitra et al.).

The reducing and oxidizing agents are present in amounts sufficient to permit an adequate free-radical reaction rate. This can be evaluated by combining all of the ingredients of the hardenable composition except for the optional filler, and observing whether or not a hardened mass is obtained. Preferably, the reducing agent is present in an amount of at least 0.01% by weight, and more preferably at least 0.1% by weight, based on the total weight (including water) of the components of the hardenable composition. Preferably, the reducing agent is present in an amount of no greater than 10% by weight, and more preferably no greater than 5% by weight, based on the total weight (including water) of the components of the hardenable composition.

Preferably, the oxidizing agent is present in an amount of at least 0.01% by weight, and more preferably at least 0.10% by weight, based on the total weight (including water) of the components of the hardenable composition. Preferably, the oxidizing agent is present in an amount of no greater than 10% by weight, and more preferably no greater than 5% by weight, based on the total weight (including water) of the components of the hardenable composition.

The reducing or oxidizing agents can be microencapsulated as described in U.S. Pat. No. 5,154,762 (Mitra et al.). This will generally enhance shelf stability of the hardenable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a hardenable composition such as described U.S. Pat. No. 5,154,762 (Mitra et al.).

Fillers

Hardenable compositions as described herein can optionally contain fillers. Fillers may be selected from one or more of a wide variety of materials suitable for incorporation in compositions used for dental applications, such as fillers currently used in dental restorative compositions, and the like.

For certain embodiments, the filler is preferably finely divided. The filler can have a unimodial or polymodial (e.g., bimodal) particle size distribution. For some embodiments, the maximum particle size (the largest dimension of a particle, typically, the diameter) of the filler is less than 50 micrometers, oftentimes less than 20 micrometers, and sometimes than 10 or even 5 micrometers. In certain embodiments, the average particle size of the filler is less than 0.1 micrometers, and sometimes less than 0.075 micrometer.

The filler can be an inorganic material. It can also be a crosslinked organic material that is insoluble in the resin system (i.e., the hardenable components), and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) filler, silane-treated silica filler, silane-treated zirconia filler, and combinations thereof are especially preferred in certain embodiments.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), WO 01/30306 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.) and U.S. Pat. No. 7,090,722 (Budd et al.); and U.S. Pat. Application Publication Nos. 2005/0252413 A1 (Kangas et al.) and 2005/0256223 A1 (Kolb et al.).

For some embodiments of the present invention that include filler (e.g., dental adhesive compositions, orthodontic primers, orthodontic sealants, and the like), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition.

For other embodiments (e.g., where the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, and more preferably at most 85% by weight filler, based on the total weight of the composition.

Miscellaneous Optional Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. 6,669,927 (Trom et al.) and U.S. Pat. Application Publication No. 2004/0151691 (Oxman et al.).

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

The present invention is illustrated by the following examples. It is to be understood that the particular examples, materials, amounts, and procedures are to be interpreted broadly in accordance with the scope and spirit of the invention as set forth herein. Unless otherwise indicated, all parts and percentages are on a weight basis, all water is deionized water, and all molecular weights are weight average molecular weight.

EXAMPLES

Test Methods

Adhesion to Uncut Enamel Test Method A

Adhesion to uncut enamel for a given test sample was evaluated by the following procedure.

Preparation of Teeth.

Bovine incisal teeth were obtained from a local slaughterhouse, the roots cut off, and the pulp removed. The teeth, free of soft tissue, were embedded in circular acrylic disks so that the labial surfaces of the teeth were exposed. The embedded teeth were stored in water at room temperature. The exposed labial surfaces of the embedded teeth were cleaned using a prophy paste prior to bonding.

Teeth Treatment.

A self-etching sealant test sample was applied with a water-moistened dental applicator brush as an approximately 1 mm thick layer over the entire exposed surface of the enamel surface. After one minute, a Victory Series upper central bracket coated with TRANSBOND XT Light Cure Adhesive (3M Unitek) was pressed down on the sealant-coated tooth surface and cured for 5 seconds on the mesial side and 5 seconds on the distal side with an ORTHOLUX LED curing light (3M Unitek). After curing, the resulting assembly was placed in a 37° C. water bath until adhesive strength was measured.

Adhesive Bond Strength Testing.

Adhesive bond strength was measured as follows on the tooth-bracket assembly. A 0.50-mm round stainless steel wire loop (e.g., Part number 211-200, 3M Unitek) was engaged under the occlusal tie wings of the bracket. Using a Qtest/5 Tester (MTS Systems), a load was applied in a shear/peel mode until the bracket debonded from the tooth. The wire attached to the tester was pulled at a rate of 5 millimeters per minute. The maximum force was recorded as the bond strength per bracket. The values reported in the Tables below are an average of 10 individual measurements that were made using 10 different adhesive coated brackets bonded to teeth. This average value was normalized for the area of the bond and is reported in units of megapascals (MPa).

Adhesion to Uncut Enamel Test Method B

Adhesion to uncut enamel for a given test sample was evaluated by the following procedure.

Preparation of Teeth.

Same as described for Adhesion to Uncut Enamel Test Method A

Teeth Treatment.

A self-etching sealant test sample was applied with a water-moistened dental applicator brush as an approximately 1.5 mm thick layer over the entire surface of an orthodontic adhesive test sample that had been coated on the base of a Victory Series upper central bracket. The bracket was immediately placed on the tooth surface and, after one minute, the bracket was pressed down on the tooth and the flash cleaned. The brackets were cured for 5 seconds (when TRANSBOND XT Light Cure Adhesive was used) or 10 seconds (when Example 3 self-adhesive orthodontic adhesive was used) with an ORTHOLUX LED curing light (3M Unitek). After curing, the resulting assembly was placed in a 37° C. water bath until adhesive strength was measured.

Adhesive Bond Strength Testing.

Adhesive bond strength was measured as follows on the tooth-bracket assembly. A 0.50-mm round stainless steel wire loop (e.g., Part number 211-200, 3M Unitek) was engaged under the occlusal tie wings of the bracket. Using a Qtest/5 Tester (MTS Systems), a load was applied in a shear/peel mode until the bracket debonded from the tooth. The wire attached to the tester was pulled at a rate of 5 millimeters per minute. The maximum force was recorded as the bond strength per bracket. The values reported in the Tables below are an average of 10 individual measurements that were made using 10 different adhesive coated brackets bonded to teeth. This average value was normalized for the area of the bond and is reported in units of megapascals (MPa).

Adhesion to Cut Enamel Test Method C

Adhesive strength to cut enamel for a given test sample was evaluated by the following procedure.

Preparation of Teeth.

For each test sample, five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the enamel. During this and subsequent grinding and polishing steps, the teeth were continuously rinsed with water. Further grinding and polishing of the teeth was carried out by mounting Grade 600 silicon carbide paper-backed abrasive on the lapidary wheel. The polished teeth were stored in deionized water and used for testing within 2 hours after polishing. The polished teeth were removed from the water and blotted dry such that the tooth surface had visible water on up to 50% of the total surface at the time of adhesive application.

Teeth Treatment.

Glass tubes, each having a diameter of 5 millimeters, were filled with FILTEK Z100 Restorative composite (available from 3M ESPE Dental Products, St. Paul, Minn.). The filled tubes were subjected to 0.275 MPa pressure for 5 minutes and irradiated with a Model XL 3000 dental curing light (3M ESPE Dental Products) for 60 seconds. The resulting cured composite was removed from the tubes and cut into 2-mm thick Z100 test buttons. One side of each button was roughened with 120-grit sandpaper. In a controlled environment of 24° C. and 50% relative humidity and within one minute of preparing a test sample, a layer of the test sample was applied with a spatula to the roughened side of the Z100 button. The button with the applied test sample facing the tooth was pressed onto the tooth surface (that had been brushed with DI water over 50% of the tooth surface) to create an assembly. The assembly was allowed to stand for an additional minute. Thereafter, the test sample layer was irradiated with a XL 3000 dental curing light for 40 seconds. The entire assembly was placed in a humidity chamber at 97% relative humidity and a temperature of 37° C. for 20 minutes. The assembly was then placed into deionized water at a temperature of 37° C. for 24 hours.

Adhesive Bond Strength Testing.

The adhesive strength of a cured test example was evaluated by mounting the assembly (described above) in a holder clamped in the jaws of an INSTRON testing machine (Instron 4505, Instron Corp. Canton, Mass.) with the polished tooth surface oriented parallel to the direction of pull. A loop of orthodontic wire (0.44-mm diameter) was placed around the Z100 button adjacent to the polished tooth surface. The ends of the orthodontic wire were clamped in the pulling jaw of the INSTRON apparatus and pulled at a crosshead speed of 2 millimeters per minute (mm/min), thereby placing the adhesive bond in shear stress. The force (measured in kilograms) at which the bond failed was recorded, and this number was converted to a force per unit area using the known surface area of the button. Each value of adhesion to enamel or adhesion to dentin represents the average of 5 replicates and is reported in the Tables in units of megapascals (MPa).

Adhesion to Cut Enamel Test Method D

The Adhesion to Cut Enamel Test Method D is similar to Test Method B except that approximately 10 milligrams of the adhesive was applied to the bracket and was then spread over the surface of the bracket. After seating on the tooth surface, the adhesive was cured for 10 seconds on the mesial side and 10 seconds on the distal side with an ORTHOLUX LED curing light (3M Unitek). Then the teeth with the bonded bracket were stored in water at 37° C. for 24 hours before testing. The wire attached to the bracket was pulled at a rate of 2 millimeters per minute.

Compressive Strength (CS) Test Method CS

Compressive strength was evaluated by first injecting a test sample into a glass tube having a 4-mm inner diameter. The ends of the glass tube were plugged with silicone plugs. The filled tubes were subjected to 0.275 megapascal (MPa) pressure for 5 minutes, irradiated with a XL 1500 curing light (3M Company) for 80 seconds, and placed in a KULZER UniXS (Kulzer, Inc., Germany) light box for 180 seconds. Five such cured samples were cut to a length of 8 mm and placed in 37° C. water for 1 day. Compressive strength was determined according to ISO Standard 7489 using an INSTRON universal tester (Instron Corp., Canton, Mass.) operated at a crosshead speed of 1 millimeter per minute (mm/min). Results were reported as the average of 5 replicates.

Diametral Tensile Strength (DTS) Test Method DTS

Diametral tensile strength was measured essentially as described above for the CS procedure, but the samples were cut to a length of 2 mm. Results are reported as the average of 5 replicates.

Color Test Method

Initial and final colors were determined using a HunterLab Ultrascan XE Spectrocolorimeter (Reston, Va.). The spectrocolorimeter was standardized using a Diffuse/8° light trap followed by a Diffuse/8° instrument standard (U3322) (L*: 98.99; a*: −0.29; b*: −0.21). The instrument standard was calibrated by direct comparison to HunterLab Master Transfer Standards which are traceable to NIST (National Institute of Standards and Technology). In this method, a small area view was used with a port size of 0.375" (9.5 mm) diameter. An uncured test sample (generally a paste) was placed in a circular mold (15-mm diameter) and a 1-mm thick section of the sample was sandwiched between 2 polyester films and measured. Cured samples were obtained by curing the test sample for 1 minute on both sides using an XL 1500 curing light (3M Company).

As part of an aging study, an uncured test sample color was measured against a white background (L*: 94.00; a*: −0.92; b*: −0.27) and a reflectance spectrum and L*a*b* color data (as described in "Principles of Color Technology," Billmeyer & Saltzman, Second Edition, 1981) were generated. Data were generated for the uncured test sample at Day 0 (with and without acidic monomers present), and after aging in the dark ("dark" means in the absence of light, e.g., stored in aluminum foil pouches) for from 7 days to 6 months at room temperature (RT; approximately 22° C. to 24° C.).

In the case of the cured test samples, reflectance spectrum and L*a*b* color data were measured at Day 0 and after aging in the dark for from 3 days to 6 months at room temperature.

Additionally, reflectance spectrum and L*a*b* color data were collected for cured test samples aged in the light (UV Light, Sun light, box used per ISO 4049 from Heraeus 7011-59000) for 24 hours in deionized (DI) water at 37° C.

The L*a*b* system is based on a 3-dimensional color space with the positive X-axis representing red, the negative X-axis representing green, the positive Y-axis representing yellow, the negative Y-axis representing blue, and the Z-axis going from zero (black) to 100 (white) with the origin at 50. Delta E is a calculation of total color change in the three color dimensions and is described by the following equation:

$$\text{Delta } E = \text{Square root}[(L_1^* - L_2^*)^2 + (a_1^* - a_2^*)^2 + (b_1^* - b_2^*)^2]$$

where subscripts "1" indicate initial state and "2" indicate final state.

The human eye can detect a color change of approximately 3 Delta E units in normal lighting conditions.

ABBREVIATIONS, DESCRIPTIONS, AND SOURCES OF MATERIALS

Unless otherwise noted, reagents and solvents were obtained from Sigma-Aldrich Corp., St. Louis, Mo. Azo dyes (Disperse Red 1, Disperse Red 13, and Sudan Black B), aminoanthraquinone dyes (Disperse Blue 3 and Solvent Blue 35), and quinizarin (1,4-dihydroxyanthraquinone) were obtained from Sigma-Aldrich Corp.

As used herein,

"TEGDMA" refers to triethyleneglycol dimethacrylate, obtained from Sartomer Co., Inc., Exton, Pa.;

"UDMA" refers to diurethane dimethacrylate, obtained under the trade designation "ROHAMERE 6661-0" from Rohm America LLC, Piscataway, N.J.;

"SR340" refers to 2-phenoxyethyl methacrylate, obtained under the trade designation SR340 from Sartomer Co., Inc., Exton, Pa.;

"BisEMA" refers to ethoxylated bisphenol A dimethacrylate, obtained from Sartomer Co., Inc., Exton, Pa.;

"GDMA-P" refers to Glycerol dimethacrylate phosphate, prepared as described in J. Dent. Res., 35, 8466 (1956);

"MHP" refers to methacryloyloxyhexyl phosphate;

"PM-2" refers to bis(methacryloxyethyl) phosphate, obtained under the trade designation KAYAMER PM-2 from Nippon Kayauku, Tokyo, Japan;

"RN-50" refers to a polymerizable nonionic surfactant obtained under the trade designation NOIGEN RN-50 from DAI-Ichi Kogyo Seiyaku Co. Ltd., Japan;

"BHT" refers to butylated hydroxytoluene;

"Zr—Si FILLER" refers to silane-treated zirconia-silica filler prepared as described in U.S. Pat. No. 4,503,169 (Randklev);

"R812S" refers to a silane-treated fumed silica obtained under the trade designation AEROSIL R812S from Cabot Corp., Tuscola, Ill.;

"TS-720" refers to a dimethyl silicone-treated fumed silica obtained under the trade designation AEROSIL TS-720 from Cabot Corp., Tuscola, Ill.;

"S/T $TiO_2$" refers to a silane-treated titanium dioxide powder, obtained under the trade designation MT-500 HD from Daicolor-Pope, Clifton, N.J.;

"IRGACURE" refers to a photoinitiator obtained under the trade designation IRGACURE 819 from Ciba Specialty Chemicals, Tarrytown, N.Y.;

"CPQ" refers to camphorquinone;

"EDMAB" refers to ethyl 4-dimethylaminobenzoate;

"EDMOA" refers to 2-ethyl-9,10-dimethoxyanthracene;

"DPIPF6" refers to diphenyliodonium hexafluorophosphate, obtained from Alfa Aesar, Ward Hill, Mass.;

"RED X64" refers to a polymeric dye obtained under the trade designation REACTINT RED X64 from Milliken Chemical, Inman, S.C. Analysis by nuclear magnetic resonance spectroscopy indicated it to be an azo dye;

"BLUE X17AB" refers to a polymeric dye obtained under the trade designation REACTINT BLUE X17AB from Milliken Chemical, Inman, S.C. Analysis by nuclear magnetic resonance spectroscopy indicated it to be an aminoanthraquinone dye;

"BLACK X95AB" refers to a polymeric dye obtained under the trade designation REACTINT BLACK X95AB from Milliken Chemical, Inman, S.C. Analysis by nuclear magnetic resonance spectroscopy indicated it to be a mixture of azo and aminoanthraquinone dyes;

"CC ACID" refers to 3-hydroxy-4-(2-hydroxy-4-sulfo-1-naphthylazo)-2-naphthalene carboxylic acid, an azo dye;

"EE" refers to ethyl eosin, a xanthene dye;

"EYB" refers to erythrosin yellowish blend, a xanthene dye mixture of 90 weight percent erythrosin B and 10 weight percent eosin Y;

"MB" refers to methylene blue, a xanthene dye;

Preparative Example 1

Preparation of MHP 1,6-Hexanediol (1000.00 g) was placed in a 1-liter 3-neck flask equipped with a mechanical stirrer and a narrow inlet tube supplying dry air into the flask. The flask was heated to 90° C., at which temperature all the compound melted. With continuous stirring, p-toluenesulfonic acid (18.95 g) followed by BHT (2.42 g) and methacrylic acid (728.32 g). The mixture was stirred and heated at 90° C. for 5 hours, during which time vacuum was applied using a water aspirator for 5-10 minutes after each approximately half hour reaction time. The reaction mixture was then allowed to cool to room temperature. The crude viscous liquid product was successively washed with 10 weight percent aqueous sodium carbonate (2×240 mL), water (2×240 mL), and saturated aqueous NaCl (100 mL). The viscous liquid was then dried using anhydrous sodium sulfate and was then isolated by vacuum filtration to give 1067 g of 6-hydroxyhexyl methacrylate as a yellow oil.

A slurry was formed by mixing $P_2O_5$ (178.66 g) and methylene chloride (500 mL) under an atmosphere of nitrogen gas in a 1-liter flask equipped with a mechanical stirrer. The flask was cooled in an ice bath for 15 minutes. With continuous stirring, 6-hydroxyhexyl methacrylate (962.82 g) was slowly added to the flask over 2 hours. After the addition was complete, the mixture was stirred in the ice bath for 1 hour then at room temperature for 2 hours. BHT (0.5 g) was added to the flask, and then the temperature was raised to reflux for 45 minutes. The mixture was then allowed to cool to room temperature. The solvent was removed under vacuum to afford 1085 g of 6-methacryloxyhexyl phosphate (MHP) as a yellow oil. Chemical characterization was by NMR analysis.

Preparative Example 2

Curable Dental Composition Including UDMA

A resin mixture was prepared having the composition given in Table 1. The components listed in Table 1 were combined using a Model DAC 150 FVZ SpeedMixer (manufactured by FlackTek, Inc., Landrum, S.C.) twice for one minute each at 3000 rpm. A curable dental composition was prepared by combining the resin mixture (19 weight percent), TS-720 (1.5 weight percent), and silane-treated quartz (79.5 weight percent; prepared as described in U.S. Pat. No. 6,960,079 (Brennan et al.)) using a SpeedMixer as described above.

TABLE 1

Resin Composition of Preparative Example 2.

| Component | Weight Percentage |
|---|---|
| SR340 | 20.10 |
| UDMA | 46.90 |
| PM-2 | 12.07 |
| MHP | 18.11 |
| BHT | 0.13 |
| CPQ | 0.31 |
| EDMAB | 0.76 |
| EDMOA | 0.31 |

TABLE 1-continued

Resin Composition of Preparative Example 2.

| Component | Weight Percentage |
|---|---|
| DPIPF6 | 0.31 |
| IRGACURE | 0.99 |

Preparative Example 3

Curable Dental Paste Including UDMA and 2 Weight Percent Azo Dye

The composition of Preparative Example 2 (5.0 g) was combined with RED X64 (0.1 g) using a Model DAC 150 FVZ SpeedMixer (manufactured by FlackTek, Inc., Landrum, S.C.) twice for one minute each at 3000 rpm to afford the product.

Preparative Example 4

Curable Dental Paste Including UDMA and 2 Weight Percent Aminoanthraquinone Dye

The composition of Preparative Example 2 (5.0 g) was combined with BLUE X17AB (0.1 g) using a Model DAC 150 FVZ SpeedMixer (manufactured by FlackTek, Inc., Landrum, S.C.) twice for one minute each at 3000 rpm to afford the product.

Examples 1-8

Dental Compositions Containing Azo Dyes

The dental compositions of Examples 1-8 were prepared by combining the components as listed in Table 2 according to the following general procedure: The curable ethylenically unsubstituted components were combined to form a uniform mixture. This mixture was then combined with the initiator system components. Finally, the fillers, dye, and other components were added and were thoroughly dispersed to afford a homogeneous dental composition. Each of the compositions of Examples 1-8 contained an azo dye. Examples 1-3 contained RED X64, Example 4 contained BLACK X95AB, Example 5 contained Disperse Red 1, Example 6 contained Disperse Red 13, Example 7 contained Sudan Black B, and Example 8 contained CC ACID. The composition of Example 1 included relatively lower levels of fillers, levels of which are similar to those that might be encountered, for example, in self-etching dental adhesives, dental sealants, orthodontic primers, and/or orthodontic sealants. The compositions of Examples 2-8 included relatively higher levels of fillers, levels of which are similar to those that might be encountered, for example, in self-etching dental restoratives and/or orthodontic adhesives.

TABLE 2

Compositions of Examples 1-8.

| | Ex. 1 | Ex. 2 | Ex. 3 | Ex. 4 | Ex. 5 | Ex. 6 | Ex. 7 | Ex. 8 |
|---|---|---|---|---|---|---|---|---|
| Dye | 0.0033 | 0.004 | 0.004 | 0.004 | 0.004 | 0.004 | 0.002 | 0.004 |
| TEGDMA | 28.00 | 0 | 0 | 0 | 0 | 0 | 0 | 0 |
| BisEMA6 | 28.00 | 17.00 | 14.20 | 17.00 | 17.00 | 17.00 | 17.00 | 17.00 |
| BHT | 0.13 | 0.073 | 0.03 | 0.073 | 0.073 | 0.073 | 0.073 | 0.073 |
| CPQ | 0.30 | 0.23 | 0.07 | 0.23 | 0.23 | 0.23 | 0.23 | 0.23 |
| EDMAB | 1.55 | 0.58 | 0.33 | 0.58 | 0.58 | 0.58 | 0.58 | 0.58 |
| DPIPF6 | 0.59 | 0.23 | 0.12 | 0.23 | 0.23 | 0.23 | 0.23 | 0.23 |
| RN-50 | 1.60 | 0 | 0 | 0 | 0 | 0 | 0 | 0 |
| GDMA-P | 0 | 3.22 | 0 | 3.22 | 3.22 | 3.22 | 3.22 | 3.22 |
| PM-2 | 27.00 | 0.47 | 5.2 | 0.47 | 0.47 | 0.47 | 0.47 | 0.47 |
| MHP | 2.60 | 2.75 | 0 | 2.75 | 2.75 | 2.75 | 2.75 | 2.75 |
| IRGACURE | 0 | 0 | 0.21 | 0 | 0 | 0 | 0 | 0 |
| TBA-BF4 | 4.10 | 0 | 0 | 0 | 0 | 0 | 0 | 0 |
| Zr—Si Filler | 0 | 75.50 | 78.30 | 75.50 | 75.50 | 75.50 | 75.50 | 75.50 |
| S/T TiO$_2$ | 0.70 | 0 | 0 | 0 | 0 | 0 | 0 | 0 |
| R812S | 5.20 | 0 | 0 | 0 | 0 | 0 | 0 | 0 |
| TS-720 | 0 | 0 | 1.5 | 0 | 0 | 0 | 0 | 0 |
| TOTAL: | 100 | 100 | 100 | 100 | 100 | 100 | 100 | 100 |

Examples 9-11 and Comparative Examples 1-5

Dental Compositions Containing Aminoanthraquinone Dyes

The compositions of Examples 9-11 and Comparative Examples (CE) 1-5 were prepared by combining the components as listed in Table 3 according to the procedure essentially as described for Examples 1-8. The dental compositions of Examples 9-11 each contained a different aminoanthraquinone dye, whereas the compositions of Comparative Examples 1-5 each contained a dye that was neither an azo dye nor an aminoanthraquinone dye. Example 9 contained BLUE X17AB, Example 10 contained Disperse Blue 3, Example 11 contained Solvent Blue 35, Comparative Example 1 contained MB, Comparative Examples 2 and 3 contained EYB, Comparative Example 4 contained EE, and comparative Example 5 contained quinizarin. The dental compositions of Examples 9-11 included relatively high levels of filler, levels of which are similar to those that might be encountered, for example, in dental self-etching restoratives and/or orthodontic adhesives.

TABLE 3

Compositions of Examples 9-11 and Comparative Examples 1-5

| | Ex. 9 | Ex. 10 | Ex. 11 | CE 1 | CE 2 | CE 3 | CE 4 | CE 5 |
|---|---|---|---|---|---|---|---|---|
| Dye | 0.004 | 0.002 | 0.00067 | 0.015 | 0.015 | 0.006 | 0.015 | 0.004 |
| BisEMA6 | 17.00 | 17.00 | 17.00 | 17.00 | 17.00 | 17.00 | 17.00 | 17.00 |
| BHT | 0.073 | 0.073 | 0.073 | 0.073 | 0.073 | 0.073 | 0.073 | 0.073 |
| CPQ | 0.23 | 0.23 | 0.23 | 0.23 | 0.23 | 0.23 | 0.23 | 0.23 |
| EDMAB | 0.58 | 0.58 | 0.58 | 0.58 | 0.58 | 0.58 | 0.58 | 0.58 |
| DPIPF6 | 0.23 | 0.23 | 0.23 | 0.23 | 0.23 | 0.23 | 0.23 | 0.23 |
| GDMA-P | 3.22 | 3.22 | 3.22 | 3.22 | 3.22 | 3.22 | 3.22 | 3.22 |
| PM-2 | 0.47 | 0.47 | 0.47 | 0.47 | 0.47 | 0.47 | 0.47 | 0.47 |
| MHP | 2.75 | 2.75 | 2.75 | 2.75 | 2.75 | 2.75 | 2.75 | 2.75 |
| Zr—Si Filler | 75.50 | 75.50 | 75.50 | 75.50 | 75.50 | 75.50 | 75.50 | 75.50 |
| TOTAL | 100 | 100 | 100 | 100 | 100 | 100 | 100 | 100 |

Examples 12-14

Two samples of the composition of Example 1 were separately evaluated for Adhesion to Uncut Enamel (A; using Test Method A), and one sample each of the compositions of Examples 1 and 2 were evaluated for Adhesion to Cut Enamel (C; using Test Method C), Compressive Strength (CS), and Diametral Tensile Strength (DTS), according to the Test Methods described herein. The results are given in Table 4. In Table 4, "n/a" means that the test was not carried out.

TABLE 4

Test Data for Examples 12-14.

| | | Test Method | | | |
|---|---|---|---|---|---|
| Example | Composition | A | C | CS | DTS |
| 12 | Example 1 | 16.9 MPa | 10.7 MPa | 293 MPa | 42 MPa |
| 13 | Example 1 | 17.5 MPa | n/a | n/a | n/a |
| 14 | Example 2 | n/a | 17.7 MPa | 327 MPa | 74 MPa |

Examples 15-16

The composition of Example 3 was evaluated for adhesion to uncut enamel (Test Method B). For Example 15, Test Method B was carried out as described above. In this Example, the composition of Example 3 showed an adhesion value of 3.8 MPa. For Example 16, Test Method B was modified to include the application of the composition of Example 1 to the bonding surface of the orthodontic bracket before the composition of Example 3 was applied. The composition of Example 1 served in this case essentially as a primer layer between the bonding surface of the bracket and the adhesive composition of Example 3. In this Example, the composition of Example 3 showed an adhesion value of 11.2 MPa.

Example 17

Determination of Final and Aged Color of a Cured Dental Composition

The composition of Example 1 was evaluated for a difference between the initial color (i.e., the color of the composition before exposure to actinic radiation), the final color (i.e., the color of the composition after exposure to actinic radiation), and the aged color (i.e., the color of the composition after aging at 37° C.). The composition of Example 1 provided a pale color that was readily visible in the uncured composition. The color of a disc of uncured composition was determined using the Color Test Method described herein. The color photobleached when the sample disc was cured using an orthodontic curing light (available under the trade designation ORTHOLUX LED CURING LIGHT from 3M Unitek, Monrovia, Calif.). The color of the disc of cured composition was determined using the Color Test Method described herein. The disc of cured composition was then aged in water in the dark at 37° C. The color of the cured disc was determined, using the Color Test Method, at 3-day, 7-day, 14-day, 21-day, and 28-day intervals. The data indicated that the cured disc continued to become less blue/more yellow up to about 14 days of aging, as evidenced by an increase in the b* value of the sample.

Example 18

Color Stability of an Uncured Dental Composition

The composition of Example 1 in the form of an uncured disc (0.020 mm thick) was evaluated for color stability, i.e., substantial retention of initial color upon exposure to ambient white light under conditions that do not result in curing of the composition. A disk of the uncured composition was exposed to ambient white light and the color of the disk was periodically qualitatively (i.e., visually) and quantitatively (i.e., using the Color Test Method described herein) evaluated. Within a total time of 20 minutes of continuous exposure to ambient light, the disk did not exhibit a visible change in color (i.e., it did not appear to photobleach) and the mean b* values were substantially unchanged.

Examples 19-22

Color Test Results for Dental Compositions with Dyes

The color of each of the compositions of Examples 1-2 and 4-8 (containing azo dyes), Examples 9-11 (containing aminoanthraquinone dyes), and Comparative Examples 1-4 (containing dyes that are neither azo dyes nor aminoanthraquinone dyes) was determined using the Color Test Method described herein. The color of each of the uncured compositions was determined after they were prepared ("Day 0", Example 19), and after they were allowed to age in the dark for one week at room temperature ("Day 7", Example 20). The color of disks of each of the cured compositions (which were cured using a dental or orthodontic curing light) was determined immediately after curing ("Day 0", Example 21), and after they were allowed to age for one week in the dark at room temperature ("Day 7", Example 22). The data (L*, a*, and b*) for each Example are given in Table 5. In Table 5, "n/a" means that the value was not calculated for that composition.

TABLE 5

Color Test Results for Compositions with Dyes.

| | Example | | | |
|---|---|---|---|---|
| | 19 | 20 | 21 | 22 |
| | L*/a*/b* | L*/a*/b* | L*/a*/b* | L*/a*/b* |
| | uncured, | uncured, | cured, | cured, |
| Composition | Day 0 | Day 7 | Day 0 | Day 7 |
| Ex. 1 | 79.3/−9.2/11.8 | 78.4/−8.9/11.1 | 89.3/−4.7/22.5 | 86.6/−4.1/19.1 |
| Ex. 2 | 67.8/−6.4/8.0 | 68.3/−5.5/8.1 | 79.1/−4.2/26.4 | 76.3/−2.1/21.8 |
| Ex. 4 | 65.6/1.2/13.7 | 64.2/1.2/12.3 | 76.7/−5.4/33.7 | 77.0/−6.1/32.6 |
| Ex. 5 | 73.1/21.9/18.0 | 73.5/21.1/18.2 | 78.8/−2.5/18.1 | 78.8/−2.3/19.6 |
| Ex. 6 | 66.6/25.2/13.0 | 66.7/25.1/13.3 | 79.8/−3.1/22.4 | 75.3/3.6/21.2 |
| Ex. 7 | 70.1/−5.2/14.8 | 69.5/−4.7/14.5 | 79.0/−2.4/20.2 | 77.9/−2.4/21.6 |
| Ex. 8 | 73.2/0.7/15.5 | 70.5/1.6/12.4 | 78.9/−2.6/19.1 | 78.0/−2.3/19.1 |
| Ex. 9 | 68.7/−9.1/12.1 | 69.3/−9.7/10.6 | 74.5/−2.1/29.2 | 71.9/−4.9/20.8 |
| Ex. 10 | 71.9/−9.8/12.7 | 71.7/−9.9/12.0 | 77.4/−1.6/24.5 | 75.6/−2.5/20.0 |
| Ex. 11 | 75.3/−13.3/16.7 | 74.3/−13.6/16.3 | 78.4/−2.2/23.2 | 77.4/−3.4/20.6 |
| CE 1 | 60.0/−27.1/−4.5 | n/a | 74.3/−3.1/9.9 | 59.1/−26.9/−11.0 |
| CE 2 | 80.3/7.9/33.1 | n/a | 79.1/−2.9/18.0 | 78.5/−0.6/24.6 |
| CE 3 | 82.9/2.2/32.0 | n/a | 81.3/−2.6/13.5 | n/a |
| CE 4 | 73.6/28.8/49.3 | n/a | 78.6/−3.1/22.3 | 74.2/10.7/40.9 |

Examples 23-24

Color Change (Delta E) of Uncured Dental Compositions with Dyes

The color change (Delta E) of each of the uncured compositions of Examples 1-2 and 4-8 (containing azo dyes), Examples 9-11 (containing aminoanthraquinone dyes), and Comparative Examples 1-4 (containing dyes that are neither azo dyes nor aminoanthraquinone dyes) was determined using the Color Test Method described herein. The color change (Delta E) of each of the uncured compositions was determined using the initial color of each uncured composition after they were prepared, the color after they were allowed to age in the dark for one week at room temperature ("Day 7", Example 23), and the color after they were allowed to age for at least 5 months in the dark at room temperature ("Extended", Example 24). The data (Delta E) for each Example are given in Table 6. In Table 5, the time of the "Extended" aging test is given for each sample. In Table 6, "n/a" means that the value was not calculated for that composition.

TABLE 6

Color Change (Delta E) for Uncured Dental Compositions with Dyes

| | Example | |
|---|---|---|
| Composition | 23 Delta E Day 7 | 24 Delta E Extended |
| Ex. 1 | 1.2 | 5.1 (5 months) |
| Ex. 2 | 1.0 | 6.7 (6 months) |
| Ex. 4 | 2.0 | 2.1 (6 months) |
| Ex. 5 | 0.9 | 11.8 (6 months) |
| Ex. 6 | 0.3 | n/a |
| Ex. 7 | 0.9 | n/a |
| Ex. 8 | 4.2 | n/a |
| Ex. 9 | 1.8 | 4.7 (6 months) |
| Ex. 10 | 0.8 | n/a |
| Ex. 11 | 1.1 | n/a |
| CE 1 | n/a | n/a |
| CE 2 | n/a | n/a |
| CE 3 | n/a | n/a |
| CE 4 | n/a | n/a |

Examples 25-28

Color Change (Delta E) of Cured Dental Compositions with Dyes

The color change (Delta E) of each of the cured compositions of Examples 1-2 and 4-8 (containing azo dyes), Examples 9-11 (containing aminoanthraquinone dyes), and Comparative Examples 1-4 (containing dyes that are neither azo dyes nor aminoanthraquinone dyes) was determined using the Color Test Method described herein. The color change (Delta E) of each of the cured compositions was determined using the initial color of each cured composition after they were cured ("Day 0", Example 25), the color after they were allowed to age for 24 hours in the dark in water at 37° C. ("Day 1", Example 26), the color after they were allowed to age for 1 week in the dark in water at 37° C. ("1 Week", Example 26), and after they were allowed to age for 3 or 6 months in the dark in water at 37° C. ("Extended", Example 24). The data (Delta E) for each Example are given in Table 7. In Table 7, the time of the "Extended" aging test is given for each sample. In Table 7, "n/a" means that the value was not calculated for that composition.

TABLE 7

Color Change (Delta E) for Cured Dental Compositions with Dyes.

| | Example | | | |
|---|---|---|---|---|
| Composition | 25 Delta E Day 0 | 26 Delta E Day 1 | 27 Delta E 1 Week | 28 Delta E Extended |
| Ex. 1 | 15 | 7.3 | 4.4 | 6.2 (3 months) |
| Ex. 2 | 22 | 6.2 | 5.7 | 1.4 (6 months) |
| Ex. 4 | 24 | 11.7 | 1.4 | 2.3 (6 months) |

TABLE 7-continued

Color Change (Delta E) for Cured Dental Compositions with Dyes.

| | Example | | | |
|---|---|---|---|---|
| Composition | 25 Delta E Day 0 | 26 Delta E Day 1 | 27 Delta E 1 Week | 28 Delta E Extended |
| Ex. 5 | 25 | 4.4 | 1.5 | n/a |
| Ex. 6 | 27 | 5.1 | 8.1 | n/a |
| Ex. 7 | 11 | 5.1 | 1.9 | n/a |
| Ex. 8 | 7 | 4.5 | 0.9 | n/a |
| Ex. 9 | 19 | 8.4 | 9.5 | 10.6 (6 months) |
| Ex. 10 | 15 | 4.4 | 4.9 | n/a |
| Ex. 11 | 13 | 4.5 | 3.1 | n/a |
| CE 1 | 28 | n/a | 35.2 | n/a |
| CE 2 | 16 | n/a | 7.0 | n/a |
| CE 3 | 19 | n/a | n/a | n/a |
| CE 4 | 38 | n/a | 23.5 | n/a |

Examples 29-34 and Comparative Example 1

Dental Compositions Containing UDMA

For Examples 29-31, mixtures of the compositions of Preparative Examples 2 and 3, in the amounts given in Table 8, were combined using a Model DAC 150 FVZ Speed-Mixer (manufactured by FlackTek, Inc., Landrum, S.C.) twice for one minute each at 3000 rpm. Each of the dental compositions of Examples 29-31 contained the azo dye at the weight percentage given in Table 8. For Examples 32-34, mixtures of the compositions of Preparative Examples 2 and 4, in the amounts given in Table 8, were combined using a Model DAC 150 FVZ SpeedMixer twice for one minute each at 3000 rpm. Each of the dental compositions of Examples 32-34 contained the aminoanthraquinone dye at the weight percentage given in Table 8. For Comparative Example 1, neither the composition of Preparative Example 3 nor the composition of Preparative Example 4 was combined with the composition of Preparative Example 2. Adhesion to cut enamel of each of the compositions of Examples 29, 30, 32, and Comparative Example 1 was determined using Test Method D as described herein. The adhesive bond strength data are given in Table 8.

TABLE 8

Compositions of Examples 29-34 and Comparative Example 1.

| Example | Preparative Example 2 | Preparative Example 3 | Preparative Example 4 | Weight percent dye | Adhesive bond strength |
|---|---|---|---|---|---|
| 29 | 5 g | 0.025 g | n/a | 0.01% | 17.4 MPa |
| 30 | 5 g | 0.05 g | n/a | 0.02% | 18.4 MPa |
| 31 | 5 g | 0.1 g | n/a | 0.04% | — |
| 32 | 5 g | n/a | 0.025 g | 0.01% | 18.1 MPa |
| 33 | 5 g | n/a | 0.05 g | 0.02% | — |
| 34 | 5 g | n/a | 0.1 g | 0.04% | — |
| CE 1 | 5 g | n/a | n/a | 0% | 18.4 MPa |

In Table 8, "n/a" means that the composition was not present in the Example, and "—" means that the data was not obtained.

Examples 35-39

Color Test Results for Dental Compositions Containing UDMA and Azo Dye

The color of each of the compositions of Examples 29-31 was determined using the Color Test Method described herein. The color of the compositions was determined after they were prepared ("Uncured", Example 32), immediately after they were cured using an ORTHOLUX LED orthodontic curing light ("Cured", Example 33), and after they were aged in water in the dark at 37° C. for three days ("Aged", Example 34). The data (L*, a*, and b*) for each Example are given in Table 9. For each of the compositions of Example 29-31, the "Cured" and "Aged" Delta E values, i.e., the difference between the initial color (i.e., the color of the composition before exposure to actinic radiation) and the final color (i.e., the color of the composition after exposure to actinic radiation, "Cured", Example 35), and the difference between the final color and the aged color (i.e., the color of the composition after aging in water in the dark at 37° C. for three days, "Aged", Example 36), respectively, were calculated. The color of each sample photobleached when the sample disc was cured using an orthodontic curing light (available under the trade designation ORTHOLUX LED CURING LIGHT from 3M Unitek, Monrovia, Calif.). The color of the disc of cured composition was determined using the Color Test Method described herein. The disc of cured composition was then aged in water in the dark at 37° C. for three days. The data are given in Table 9. In Table 9, "n/a" means that the data was not obtained or was not calculated. Under the curing conditions, the compositions of Examples 32-34 did not exhibit high Delta E values.

clarity of understanding only. No unnecessary limitations are to be understood there from. The invention is not limited to the exact details shown and described, for variations obvious to one skilled in the art will be included within the invention defined by the claims.

What is claimed is:

1. A method for treating an oral surface, the method comprising:
    applying a hardenable dental composition to the oral surface, wherein the hardenable dental composition comprises:
        a hardenable component;
        an initiator for initiating hardening of the hardenable dental composition;
        an acidic component having a $pK_a$ of less than 4.5; and
        a photobleachable dye is aminoanthraquinone dyes, wherein the photobleachable dye is at least partially soluble in the hardenable dental composition;
    hardening the hardenable dental composition; and
    observing the color of the hardened dental composition immediately after hardening and observing the aged color of the hardened dental composition after aging for at least 3 days at or near body temperature after hardening to determine that the aged color is substantially the same as the color immediately after hardening.

TABLE 9

Color Test Results for Examples 35-39.

| Example | Color Data | Example 29 | Example 30 | Example 31 | Example 32 | Example 33 | Example 34 |
|---|---|---|---|---|---|---|---|
| 35 | L*/a*/b* Uncured | 58.1/-6.2/-18.8 | 52.0/-2.06/-23.3 | 45.8/1.9/23.9 | 67.3/3.46/3.6 | 59.2/6.6/-1.9 | 49.7/3.2/-12.2 |
| 36 | L*/a*/b* Cured | 79.9/-8.0/-5.5 | 77/-8.7/1.9 | 61.6/-9.4/-13.9 | 65.9/1.9/4.3 | 55.5/7.2/-1.1 | 46.6/4.2/-7.0 |
| 37 | L*/a*/b* Aged | 68.7/-5.3/-5.5 | 62.9/-3.0/-11.1 | 55.7/0.2/-13.8 | n/a | n/a | n/a |
| 38 | Delta E, Cured | 32.6 | 36.1 | 21.8 | 2.2 | 3.8 | 6.1 |
| 39 | Delta E, Aged | 15.8 | 20 | 11.3 | n/a | n/a | n/a |

Examples 40-42 and Comparative Example 2

Bond Strength of Dental Compositions Containing UDMA

Each of the composition of Examples 29, 30, 32, and Preparative Example 2 (Examples 40-42 and Comparative Example 2, respectively) were evaluated for Adhesion to Uncut Enamel using Test Method D. The adhesive bond strength data are given in Table 10.

TABLE 10

Adhesive Bond Strength Data for Examples 40-42 and Comparative Example 2.

| Example | Adhesive | Adhesive bond strength |
|---|---|---|
| 40 | Example 29 | 17.4 MPa |
| 41 | Example 30 | 18.4 MPa |
| 42 | Example 32 | 18.1 MPa |
| CE 2 | Preparative Example 2 | 18.4 MPa |

The complete disclosure of all patents, patent applications, and publications, and electronically available material cited herein are incorporated by reference. The foregoing detailed description and examples have been given for 2. The method of claim 1 wherein the acidic component has a $pK_a$ of less than 4.

3. The method of claim 2 wherein the acidic component has a $pK_a$ of less than 3.

4. The method of claim 1 wherein the acidic component comprises phosphoric acid functionality, phosphonic acid functionality, sulfonic acid functionality, or combinations thereof.

5. The method of claim 1 wherein the acidic component is the same as the hardenable component.

6. The method of claim 1 wherein the acidic component is different than the hardenable component.

7. The method of claim 1 further comprising adhering an orthodontic appliance to the tooth structure having the hardened dental composition thereon.

8. The method of claim 1 wherein the aminoanthroquinone dye is selected from the group consisting of monoaminoanthraquinone dyes and diaminoanthraquinone dyes.

9. The method of claim 8 wherein the diaminoanthraquinone dyes are of the formula (Formula I):

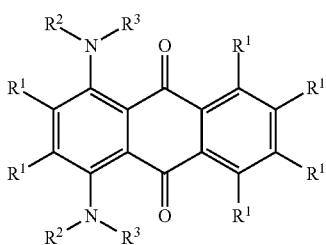

wherein each $R^1$, $R^2$, and $R^3$ is independently hydrogen or an organic group.

10. The method of claim 9 wherein each $R^1$ and each $R^2$ is hydrogen, and each $R^3$ is an organic group.

11. The method of claim 1 wherein the initiator is a photoinitiator.

12. The method of claim 11 wherein hardening the hardenable dental composition comprises exposing the hardenable dental composition to actinic radiation.

13. A method for treating a tooth structure, the method comprising:
applying a hardenable dental composition to the tooth structure, wherein the hardenable dental composition has an initial color prior to hardening and comprises:
a hardenable component;
an initiator for initiating hardening of the hardenable dental composition;
an acidic component having a $pK_a$ of less than 4.5; and
a photobleachable dye is aminoanthraquinone dyes, wherein the photobleachable dye is at least partially soluble in the hardenable dental composition;
hardening the hardenable dental composition to provide a hardened dental composition having a final color immediately after hardening, the final color being different than the initial color; and
observing the aged color of the hardened dental composition after aging for at least 3 days at or near body temperature after hardening to determine that the aged color is substantially the same as the final color.

14. The method of claim 13 wherein the change in color from the initial color to the final color has a $\Delta E^*$ of greater than 10.

15. The method of claim 13 wherein the final color is able to transmit the color of an underlying surface.

16. The method of claim 13 wherein the hardenable dental composition is an adhesive, a primer, a sealant, a restorative, a coating, a liner, or a cement.

17. The method of claim 13 wherein the hardenable dental composition is self-etching.

18. A method for treating a tooth structure, the method comprising:
applying a hardenable dental composition to the tooth structure, wherein the hardenable dental composition has an initial color prior to exposure to actinic radiation and comprises:
an ethylenically unsaturated compound with acid functionality and having a $pK_a$ of less than 4.5;
an ethylenically unsaturated compound without acid functionality;
a hardener for initiating hardening of the hardenable dental composition; and
a photobleachable dye is aminoanthraquinone dyes, wherein the photobleachable dye is at least partially soluble in the hardenable dental composition;
irradiating the hardenable dental composition to provide a hardened dental composition having a final color, the final color being different than the initial color; and
observing the aged color of the hardened dental composition after aging for at least 3 days at or near body temperature after hardening to determine that the aged color is substantially the same as the final color.

19. The method of claim 18 wherein the ethylenically unsaturated compound without acid functionality is selected from the group consisting of triethyleneglycol dimethacrylate, diurethane dimethacrylate, 2-phenoxyethyl methacrylate, ethoxylated bisphenol A dimethacrylates, and combinations thereof.

20. The method of claim 18 wherein the hardener comprises a sensitizing compound different than the photobleachable dye.

21. The method of claim 18 wherein the hardener comprises a sensitizing compound, an electron donor, and an iodonium salt.

22. The method of claim 21 wherein the sensitizing compound is different than the photobleachable dye.

* * * * *

UNITED STATES PATENT AND TRADEMARK OFFICE
CERTIFICATE OF CORRECTION

PATENT NO. : 9,943,465 B2  
APPLICATION NO. : 12/517739  
DATED : April 17, 2018  
INVENTOR(S) : Afshin Falsafi et al.

Page 1 of 1

It is certified that error appears in the above-identified patent and that said Letters Patent is hereby corrected as shown below:

In the Specification

Column 1,
Line 10, approx., Delete "Dec. 7, 2007," and insert -- Dec. 12, 2007, --, therefor.

Column 2,
Line 22, Delete "neat" and insert -- near --, therefor.

Column 6,
Line 34, approx., Delete "tetraminoanthraquinone" and insert -- tetraaminoanthraquinone --, therefor.

Column 7,
Lines 46-47, Delete "1-napthylamine" and insert -- 1-naphthylamine --, therefor.

Column 9,
Line 8, Delete "fumeric" and insert -- fumaric --, therefor.

In the Claims

Column 34,
Lines 61-62, In Claim 8, delete "aminoanthroquinone" and insert -- aminoanthraquinone --, therefor.

Signed and Sealed this  
Eighth Day of January, 2019

Andrei Iancu  
*Director of the United States Patent and Trademark Office*